(12) United States Patent
Stella et al.

(10) Patent No.: US 11,035,851 B2
(45) Date of Patent: Jun. 15, 2021

(54) METHOD OF IDENTIFYING COSMETIC AGENTS FOR MOISTURIZING SKIN

(71) Applicant: The Procter & Gamble Company, Cincinnati, OH (US)

(72) Inventors: Qing Stella, Cincinnati, OH (US); Michael Keith Robinson, West Chester, OH (US); Kevin John Mills, Goshen, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 375 days.

(21) Appl. No.: 15/590,598

(22) Filed: May 9, 2017

(65) Prior Publication Data
US 2017/0322200 A1 Nov. 9, 2017

Related U.S. Application Data

(60) Provisional application No. 62/333,336, filed on May 9, 2016.

(51) Int. Cl.
*G01N 33/50* (2006.01)
*C12Q 1/6876* (2018.01)
*G01N 33/68* (2006.01)

(52) U.S. Cl.
CPC ....... *G01N 33/5023* (2013.01); *C12Q 1/6876* (2013.01); *G01N 33/5044* (2013.01); *G01N 33/6881* (2013.01); *C12Q 2600/136* (2013.01); *C12Q 2600/148* (2013.01); *C12Q 2600/158* (2013.01); *G01N 2500/10* (2013.01); *G01N 2570/00* (2013.01)

(58) Field of Classification Search
None
See application file for complete search history.

(56) References Cited

PUBLICATIONS

Wu (Journal of Pathology 2001 vol. 195 pp. 53-65) (Year: 2001).*
Evans (Nature 2004 vol. 429, pp. 464-468) (Year: 2004).*

* cited by examiner

*Primary Examiner* — Katherine D Salmon
(74) *Attorney, Agent, or Firm* — John G. Powell

(57) ABSTRACT

Methods of identifying potential skin moisturizing actives for the treatment of dry skin and method of formulating a moisturizing skin care composition using actives identified by the method. Moisturizing agents can be identified by comparing the transcriptional profile of a skin tissue sample contacted by a test agent to a negative or positive control to determine if the regulation of certain genes corresponds to the appropriate direction of regulation indicated by the control. Agents identified as skin moisturizing agents can then be incorporated into a skin moisturizing composition.

8 Claims, 5 Drawing Sheets

Gene expression regulations within Dry Skin population

| Genes | Dry: Winter vs. summer | | SLS on dry vs. dry BL | |
|---|---|---|---|---|
| | LFC | p value | LFC | p value |
| REL | -0.0981 | 2.10E-03 | -0.1082 | 3.10E-04 |
| ITGB1 | -0.2894 | 3.30E-06 | -0.1294 | 1.91E-02 |
| TGFBR2 | -0.1578 | 4.39E-03 | -0.0624 | 3.60E-02 |
| YY1AP1 | 0.0675 | 1.04E-04 | 0.028 | 1.68E-01 |
| TERT | -0.0257 | 6.47E-03 | -0.0268 | 4.57E-03 |
| MDM2 | 0.1358 | 4.44E-06 | 0.0531 | 5.85E-02 |
| MAPK3 | 0.0883 | 2.16E-06 | 0.1096 | 6.51E-08 |
| CASP3 | -0.1232 | 2.09E-07 | 0.0222 | 4.10E-01 |
| LAMC2 | -0.1068 | 1.82E-03 | -0.1222 | 2.32E-04 | significant down regulating
significant up regulating
statistically significant p value

BOLD genes are significant for both conditions (seasonal and surfactant treatment)

FIG. 1

Gene expression regulation: seasonal effect comparison of dry and healthy skin populations

| Genes | Dry: Winter vs. summer | | Healthy: Winter vs. summer | |
|---|---|---|---|---|
| | LFC | p value | LFC | p value |
| REL | -0.0981 | 2.10E-03 | -0.0763 | 4.93E-02 |
| ITGB1 | -0.2894 | 3.30E-06 | -0.4188 | 1.00E-06 |
| TGFBR2 | -0.1578 | 4.39E-03 | -0.2216 | 7.93E-03 |
| YY1AP1 | 0.0675 | 1.04E-04 | 0.0938 | 4.72E-05 |
| TERT | -0.0257 | 6.47E-03 | -0.0067 | 6.67E-01 |
| MDM2 | 0.1358 | 4.44E-06 | 0.0541 | 2.04E-01 |
| MAPK3 | 0.0883 | 2.16E-06 | 0.0733 | 6.47E-03 |
| CASP3 | -0.1232 | 2.09E-07 | -0.14 | 3.54E-05 |
| LAMC2 | -0.1068 | 1.82E-03 | -0.0421 | 3.49E-01 |

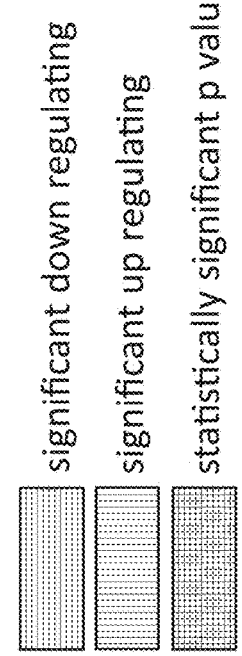

significant down regulating
significant up regulating
statistically significant p value

BOLD genes are significant for dry skin seasonal effect only

FIG. 2

Gene expression regulation: drying agent effect comparison of dry and healthy skin populations

| Genes | SLS on dry vs. dry BL | | Healthy: SLS vs. BL | |
|---|---|---|---|---|
| | LFC | p value | LFC | p value |
| REL | -0.1082 | 3.10E-04 | -0.1091 | 7.68E-03 |
| ITGB1 | -0.1294 | 1.91E-02 | -0.305 | 6.77E-04 |
| TGFBR2 | -0.0624 | 3.60E-02 | -0.2465 | 6.13E-03 |
| YY1AP1 | 0.028 | 1.68E-01 | 0.0369 | 1.47E-01 |
| TERT | -0.0268 | 4.57E-03 | -0.0199 | 1.40E-01 |
| MDM2 | 0.0531 | 5.85E-02 | 0.0362 | 5.68E-01 |
| MAPK3 | 0.1096 | 6.51E-08 | 0.0373 | 2.21E-01 |
| CASP3 | 0.0222 | 4.10E-01 | -0.0175 | 4.81E-01 |
| LAMC2 | -0.1222 | 2.32E-04 | -0.0661 | 2.10E-01 | significant down regulating
significant up regulating
statistically significant p value

BOLD Unique gene to dry skin under surfactant treatment condition

FIG. 3

Gene expression regulation reversal: Known Moisturizing Active vs. SLS treated Dry Skin

| Genes | Reversal for SLS treated dry skin vs. active in DMSO | | | | | | | SLS treated dry skin vs. dry BL | |
|---|---|---|---|---|---|---|---|---|---|
| | Glycerin* | Reversal | ZPT** | Reversal | Monoolein* | Reversal | Vem 1000* | Reversal | LFC |
| REL | 0.1370 | X | -0.0240 | | -0.6280 | | 0.0680 | X | -0.1082 |
| ITGB1 | -0.1917 | | 0 | | 0.0690 | X | -0.0100 | | -0.1294 |
| TGFBR2 | -0.2299 | | -0.0657 | | 0.0905 | X | 0.1810 | X | -0.0624 |
| YY1AP1 | 0.0551 | | 0.0057 | | 0.0337 | | 0.0070 | | 0.028 |
| TERT | 0.0145 | X | 0.0183 | X | All Absent | | -0.7090 | | -0.0268 |
| MDM2 | -0.4551 | | -0.0720 | | -0.0173 | | 0.1035 | | 0.0531 |
| MAPK3 | -0.0123 | X | 0.0080 | | 0.0185 | | -0.1690 | X | 0.1096 |
| CASP3 | -0.0771 | | 0.0150 | | -0.0645 | | 0.2680 | | 0.0222 |
| LAMC2 | 0.1035 | X | -0.0037 | | -0.1178 | | -0.0513 | | -0.1222 | significant down regulating
significant up regulating
statistically significant p value

BOLD Unique gene reversal is triggered by more than one active.

FIG. 4

Gene expression regulation reversal: Known Moisturizing Active vs. Dry Skin Seasonal Effect

| Genes | Glycerin* | Reversal | ZPT** | Reversal | onoolein* | Reversal | em 1000* | Reversal | LFC Dry: Winter vs. summer |
|---|---|---|---|---|---|---|---|---|---|
| REL | 0.1370 | x | -0.0240 | | -0.6280 | | 0.0680 | x | -0.0981 |
| ITGB1 | -0.1917 | | 0 | | 0.0690 | x | -0.0100 | | -0.2894 |
| TGFBR2 | -0.2299 | | -0.0657 | | 0.0905 | x | 0.1810 | x | -0.1578 |
| YY1AP1 | 0.0551 | | 0.0057 | | 0.0337 | | 0.0070 | | 0.0675 |
| TERT | 0.0145 | x | 0.0183 | x | All Absent | | -0.7090 | | -0.0257 |
| MDM2 | -0.4551 | x | -0.0720 | x | -0.0173 | x | 0.1035 | x | 0.1358 |
| MAPK3 | -0.0123 | x | 0.0080 | | 0.0185 | | -0.1690 | x | 0.0883 |
| CASP3 | -0.0771 | | 0.0150 | x | -0.0645 | | 0.2680 | x | -0.1232 |
| LAMC2 | 0.1035 | x | -0.0037 | | -0.1178 | | -0.0513 | | -0.1068 | significant down regulating
significant up regulating
statistically significant p value

BOLD Unique gene reversal is triggered by more than one active.

FIG. 5

METHOD OF IDENTIFYING COSMETIC AGENTS FOR MOISTURIZING SKIN

BACKGROUND

Skin is a complex, multi-layered and dynamic system that provides a protective covering defining the interactive boundary between an organism and the environment. It is the largest organ of the body and is vitally important to both our health and our self image. The skin comprises three principal layers, the epidermis, the dermis, and a layer of subcutaneous fat. The majority of cells in the epidermis are keratinocytes that produce a family of proteins called keratins. Keratins contribute to the strength of the epidermis. The epidermis itself may be divided into multiple layers with the outermost layer referred to as the stratum corneum, and the innermost layer referred to as the basal layer. All epidermal cells originate from the basal layer and undergo a process known as differentiation as they gradually displace outward to the stratum corneum, where they fuse into squamous sheets and are eventually shed. In healthy, normal skin, the rate of production equals the rate of shedding (desquamation).

While non-diseased skin is generally free of major conditions like disease, infection, or fungus, people with non-diseased skin can still suffer from dryness. Accordingly, it would be desirable to identify new actives for increasing the skin hydration of people that suffer from dry skin. The identification of new skin moisturizing actives often requires clinical studies to demonstrate efficacy. In these clinical studies, the affects of potential skin moisturizing actives on physical properties related to dry skin are measured using objective tools and techniques. These objective tools and techniques to determine new skin moisturizing actives include: dry skin grading to measure the reduction of visual dryness and redness; reduction in trans-epidermal water loss (TEWL), increased skin hydration, increased elastic extension, increased elastic recovery, and increased firmness, as compared to normal healthy control skin. However, these clinical studies are often prohibitively time-consuming and expensive to test screen a large number of potential skin moisturizing actives. Additionally, the objective tools and techniques that are used in these clinical studies to demonstrate the effects of the potential actives on the physical properties related to dry skin are currently not effective for in vitro screening methods.

Furthermore, certain patient populations have inherently dry skin, while other patient populations have inherently normal moisturized skin. Compounding the issue even further, dry skin changes with the seasons. Typically, dry skin is exacerbated in the winter season and is alleviated in the summer season. These changes in the severity of dry skin due to seasonal effects further complicate identifying new skin moisturizing actives using clinical studies, as clinical studies are forced to occur during the winter months.

Conventional in vitro studies of biological responses to potential cosmetic agents involve testing hundreds or thousands of potential agents in various cell types before an agent that gives the desired result can be identified and moved into a next stage of testing. However, such studies can be hindered by the complex or weakly detectable responses typically induced and/or caused by cosmetic agents. Such weak responses arise, in part, due to the great number of genes and gene products involved, and cosmetic agents may affect multiple genes in multiple ways. Moreover, the degree of bioactivity of cosmetic agents may differ for each gene and be difficult to quantify.

Furthermore, traditional biomarkers, such as cytokines and natural moisturizing factors (NMFs), do not distinguish between subjects with inherently dry skin and subjects with inherently normal moisturized skin. Additionally, most of such studies have not taken into account seasonal effects on the severity of dry skin, and how these seasonal effects influence the efficacy of the potential skin moisturizing agents. Thus, there are currently no methods available for identifying new skin moisturizing actives that can more specifically and efficaciously target the dry skin of particular patient populations, such as subjects with inherently dry skin, subjects with inherently dry skin that is further exacerbated by seasonal effects (e.g. during the winter season), subjects with inherently dry skin that is further exacerbated by treatment with a drying agent (e.g. a surfactant such as sodium lauryl sulphate (SLS)), subjects with inherently normal moisturized skin but with dry skin caused by seasonal effects, and subjects with inherently normal moisturized skin but with dry skin caused by treatment with a drying agent.

Therefore, although many skin care agents are known, an ongoing need exists for improved, sensitive, and predicative screening methods to accurately identify new skin moisturizing actives that not only provide for the treatment of dry skin, but that can also more specifically and efficaciously target the dry skin of particular patient populations during certain seasons. There is also a need to identify additional cosmetic agents that provide similar or improved benefits as compared to existing products but which are easier to formulate, produce, and/or market.

SUMMARY

Accordingly, the present invention provides novel methods useful for the screening and generation of potential skin moisturizing actives for the treatment of dry skin. Through various experiments and genomics and bioinformatics analysis, the present inventors have determined that it is possible to derive novel and unique biomarker panels for use in developing novel screening methods for identifying cosmetic test agents as effective skin moisturizers. These unique biomarker panels may serve as indicators of previously unidentified pathways associated with skin hydration, and thus can provide opportunities for identifying new classes of cosmetic agents.

In certain embodiments, the methods allow for the screening of cosmetic test agents that act as skin moisturizing actives for the treatment of dry skin. These novel methods also allow for identification of new cosmetic agents that can be screened for their selective treatment of dry skin and for the specific targeting of the dry skin of particular populations. Examples of the dry skin of particular populations include subjects with inherently dry skin, subjects with inherently dry skin that is further exacerbated by seasonal effects (e.g. the winter season), subjects with inherently dry skin that is further exacerbated by treatment with a drying agent (e.g. sodium lauryl sulphate (SLS)), subjects with inherently normal moisturized skin but with dry skin caused by seasonal effects, and subjects with inherently normal moisturized skin but with dry skin caused by treatment with a drying agent. Thus, the invention provides methods uniquely suited for identifying skin moisturizing agents that are most suitable for desired treatment targets. Additionally, these methods are particularly useful as they may serve as indicators of previously unidentified pathways associated with skin hydration, and thus can provide opportunities for identifying new classes of cosmetic agents.

According to one embodiment of the invention, a screening method for identifying a cosmetic test agent as skin moisturizer of human skin is provided. The method comprises: (a) contacting a skin tissue sample with a cosmetic test agent; (b) generating a transcriptional profile for the skin tissue sample, wherein the transcriptional profile comprises data related to the transcription of at least two genes selected from REL, ITGB1, TGFBR2, YY1AP1, MAP3K, CASP3, TERT, MDM2, LAMC2; and (c) comparing the transcriptional profile for the skin tissue sample to a control transcriptional profile. In certain embodiments, the control transcriptional profile is a positive control. In such embodiments, the method further comprises: (d) identifying the cosmetic test agent as a skin moisturizing agent for human skin when the transcriptional profile for the skin tissue sample and the control transcriptional profile are concordant. In other embodiments, the control transcriptional profile is a negative control. In such embodiments, the method further comprises: (d) identifying the cosmetic test agent as a skin moisturizing agent for human skin when the transcriptional profile for the skin tissue sample and the control transcriptional profile are discordant.

Other embodiments are directed to a screening method for identifying a cosmetic test agent as a skin moisturizing agent. The method comprises: (a) contacting a first skin tissue sample with a cosmetic test agent; (b) contacting a second skin tissue sample with a positive control agent; (c) generating a transcriptional profile for each of the first and second skin tissue samples, wherein the transcriptional profile comprises data related to the transcription of at least two genes selected from REL, ITGB1, TGFBR2, YY1AP1, MAP3K, CASP3, TERT, MDM2, LAMC2. In certain embodiments, the control transcriptional profile is a positive control. In such embodiments, the method further comprises: (d) identifying the cosmetic test agent as a skin moisturizing agent for human skin when the transcriptional profile for the skin tissue sample and the control transcriptional profile are concordant. In other embodiments, the control transcriptional profile is a negative control. In such embodiments, the method further comprises: (d) identifying the cosmetic test agent as a skin moisturizing agent for human skin when the transcriptional profile for the skin tissue sample and the control transcriptional profile are discordant.

Additional embodiments are directed to a screening method for identifying a cosmetic test agent as a skin moisturizing agent. The method comprises: (a) contacting a skin tissue sample with a cosmetic test agent; (b) generating a transcriptional profile for the skin tissue sample, wherein the transcriptional profile comprises data related to the transcription of at least two genes selected from REL, ITGB1, TGFBR2, MAP3K, CASP3, TERT, MDM2, LAMC2; and (c) comparing the transcriptional profile for the skin tissue sample to a control transcriptional profile. In certain embodiments, the control transcriptional profile is a positive control. In such embodiments, the method further comprises: (d) identifying the cosmetic test agent as a skin moisturizing agent for human skin when the transcriptional profile for the skin tissue sample and the control transcriptional profile are concordant. In other embodiments, the control transcriptional profile is a negative control. In such embodiments, the method further comprises: (d) identifying the cosmetic test agent as a skin moisturizing agent for human skin when the transcriptional profile for the skin tissue sample and the control transcriptional profile are discordant.

Further embodiments are directed to a screening method for identifying a cosmetic test agent as a skin moisturizing agent. The method comprises: (a) contacting a first skin tissue sample with a cosmetic test agent; (b) contacting a second skin tissue sample with a positive control agent; and (c) generating a transcriptional profile for each of the first and second skin tissue samples, wherein the transcriptional profile comprises data related to the transcription of at least two genes selected from REL, ITGB1, TGFBR2, MAP3K, CASP3, TERT, MDM2, LAMC2. In certain embodiments, the control transcriptional profile is a positive control. In such embodiments, the method further comprises: (d) identifying the cosmetic test agent as a skin moisturizing agent for human skin when the transcriptional profile for the skin tissue sample and the control transcriptional profile are concordant. In other embodiments, the control transcriptional profile is a negative control. In such embodiments, the method further comprises: (d) identifying the cosmetic test agent as a skin moisturizing agent for human skin when the transcriptional profile for the skin tissue sample and the control transcriptional profile are discordant Other embodiments are directed to methods of formulating a moisturizing skin care composition for human skin. The method of formulating comprises identifying a cosmetic test agent as effective for moisturizing skin according to the presently-disclosed screening methods and combining an effective amount of the cosmetic agent with a dermatologically acceptable carrier to produce the skin care composition.

These and additional objects, embodiments, and aspects of the invention will become apparent by reference to the Figures and Detail Description below.

BRIEF DESCRIPTION OF THE FIGURES

FIG. 1 depicts representative data demonstrating the seasonal effect comparison on gene expression regulation on subjects with inherently dry skin and the drying agent effect comparison on subjects with inherently dry skin.

FIG. 2 depicts representative data demonstrating the seasonal effect comparison on gene expression regulation between subjects with inherently dry skin and subjects with inherently normal moisturized skin.

FIG. 3 depicts representative data demonstrating the seasonal effect comparison on gene expression regulation between subjects with inherently dry skin and subjects with inherently normal moisturized skin.

FIG. 4 depicts representative data for the validation of the unique genes with known dry skin actives, and more particularly to the reversal of the drying agent effect with known skin moisturizing actives on gene expression in subjects with inherently dry skin.

FIG. 5 depicts representative data for the validation of the unique genes with known dry skin actives, and more particularly to the reversal of the drying seasonal effect with known skin moisturizing actives on gene expression in subjects with inherently dry skin.

DETAILED DESCRIPTION

Unless otherwise defined, all technical and scientific terms used herein have the same meaning as commonly understood by one of ordinary skill in the art to which this invention pertains. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

"Biomarker" refers to any biological molecules (e.g. genes, proteins, lipids, metabolites) that can, singularly or collectively, reflect the current or predict future state of a biological system. Thus, as used herein, various biomarkers ("biomarker panel") can be indicators of a quality of skin in terms of skin hydration, among several other properties. Biomarkers and biomarker panels can be derived from various sources of data, including but not limited to, from in vitro testing, in vivo testing, and combinations thereof. Non-limiting examples of biomarkers of interest include data related to the expression of at least one of REL, ITGB1, TGFBR2, YY1AP1, MAP3K, CASP3, TERT, MDM2, and LAMC2. For example, biomarkers of interest include the levels of at least one of: v-rel avian reticuloendotheliosis viral oncogene homolog (REL); integrin beta-1 (ITGB1); transforming growth factor beta receptor II (TGFBR2); YY1-associated protein 1 (YY1AP1); mitogen-activated protein kinase 3 (MAP3K); caspase 3, apoptosis-related cysteine peptidase (CASP3); telomerase reverse transcriptase (TERT); mdm2 p53 binding protein homolog (MDM2); and laminin, gamma 2 (LAMC2). Additionally, non-limiting examples of biomarkers of interest include date related to the transcription of at least one of REL, ITGB1, TGFBR2, YY1AP1, MAP3K, CASP3, TERT, MDM2, and LAMC2. For example, biomarkers of interest include the levels of messenger RNA ("mRNA") associated with the expression and/or regulation of at least one of REL, ITGB1, TGFBR2, YY1AP1, MAP3K, CASP3, TERT, MDM2, and LAMC2. The response of skin to treatment with compositions, including skin moisturizing compositions, can be assessed by measuring one or more biomarkers. The genes and proteins disclosed herein correspond to their respective known sequences as of May 6, 2016.

The term "keratinous tissue," as used herein, refers to keratin-containing layers disposed as the outermost protective covering of mammals which includes, but is not limited to, skin, hair, nails, cuticles, horns, claws, beaks, and hooves. With respect to skin, the term refers to one or all of the dermal, hypodermal, and epidermal layers, which includes, in part, keratinous tissue.

"Skin" means the outermost protective covering of mammals that is composed of cells such as keratinocytes, fibroblasts and melanocytes. Skin includes an outer epidermal layer and an underlying dermal layer. Skin may also include hair and nails as well as other types of cells commonly associated with skin, such as, for example, myocytes, Merkel cells, Langerhans cells, macrophages, stem cells, sebocytes, nerve cells and adipocytes.

"Non-diseased skin" refers to skin that is generally free of disease, infection, and/or fungus. As used herein, dry skin is considered to be included in non-diseased skin.

"Dry skin" is usually characterized as rough, scaly, and/or flaky skin surface, especially in low humidity conditions and is often associated with the somatory sensations of tightness, itch, and/or pain "Inherently dry skin" or "subjects with inherently dry skin" refers to human skin or humans with skin, respectively, having a dry skin grade of $\geq 2.5$. The dry skin grade is determined by a qualified grader according to the procedures described in the examples. In certain aspects, "inherently dry skin refers to human skin with a dry skin grade of $\geq 2.5$ and <4.0. In specific aspects, the dry skin grade is determined during the winter season (e.g., November-March), while in other aspects the dry skin is determined during the summer season e.g. June-August). If other aspects, the dry skin grade is determined after challenge with a surfactant (e.g. SLS).

"Inherently normal moisturized skin" or "subjects with inherently normal moisturized skin" refers to human skin or humans with skin, respectively, having a dry skin grade of <1.0. The dry skin grade is determined by a qualified grader according to the procedures described in the examples. In specific aspects, the dry skin grade is determined during the winter season (e.g., November-March), while in other aspects the dry skin is determined during the summer season e.g. June-August). If other aspects, the dry skin grade is determined after challenge with a surfactant (e.g. SLS).

As used herein, the terms "cosmetic agent" or "cosmetic test agent" mean any substance, as well any component thereof, intended to be rubbed, poured, sprinkled, sprayed, introduced into, or otherwise applied to a mammalian body or any part thereof. Cosmetic agents may include substances that are Generally Recognized as Safe (GRAS) by the US Food and Drug Administration, food additives, and materials used in non-cosmetic consumer products including over-the-counter medications. In some embodiments, cosmetic agents may be incorporated in a cosmetic composition comprising a dermatologically acceptable carrier suitable for topical application to skin. A cosmetic agent includes, but is not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are known to induce or cause at least one effect (positive or negative) on skin tissue and are discovered, using the provided methods and systems, to induce or cause at least one previously unknown effect (positive or negative) on the skin tissue; and (iii) chemicals, compounds, small molecules, extracts, formulations, or combinations thereof that are not known have an effect on skin tissue and are discovered, using the provided methods and systems, to induce or cause an effect on skin tissue.

Some examples of cosmetic agents or cosmetically actionable materials can be found in: the PubChem database associated with the National Institutes of Health, USA; the Ingredient Database of the Personal Care Products Council; and the 2010 International Cosmetic Ingredient Dictionary and Handbook, 13th Edition, published by The Personal Care Products Council; the EU Cosmetic Ingredients and Substances list; the Japan Cosmetic Ingredients List; the Personal Care Products Council, the SkinDeep database; the FDA Approved Excipients List; the FDA OTC List; the 20 Japan Quasi Drug List; the US FDA Everything Added to Food database; EU Food Additive list; Japan Existing Food Additives, Flavor GRAS list; US FDA Select Committee on GRAS Substances; US Household Products Database; the Global New Products Database (GNPD) Personal Care, Health Care, Food/Drink/Pet and Household database; and from suppliers of cosmetic ingredients and botanicals.

Other non-limiting examples of cosmetic agents include botanicals (which may be derived from one or more of a root, stem bark, leaf, seed or fruit of a plant). Some botanicals may be extracted from a plant biomass (e.g., root, stem, bark, leaf, etc.) using one more solvents. Botanicals may comprise a complex mixture of compounds and lack a distinct active ingredient. Another category of cosmetic agents are vitamin compounds and derivatives and combinations thereof, such as a vitamin B3 compound, a vitamin B5 compound, a vitamin B6 compound, a vitamin B9 compound, a vitamin A compound, a vitamin C compound, a vitamin E compound, and derivatives and combinations thereof (e.g., retinol, retinyl esters, niacinamide, folic acid, panthenol, ascorbic acid, tocopherol, and tocopherol acetate). Other non-limiting examples of cosmetic agents include sugar amines, phytosterols, hexamidine, hydroxy acids, ceramides, amino acids, and polyols.

As used herein, the term "microarray" refers broadly to any ordered array of nucleic acids, oligonucleotides, proteins, small molecules, large molecules, and/or combinations thereof on a substrate that enables gene expression profiling of a biological sample. Non-limiting examples of microarrays are available from Affymetrix, Inc.; Agilent Technologies, Inc.; Ilumina, Inc.; GE Healthcare, Inc.; Applied Biosystems, Inc.; Beckman Coulter, Inc.; etc.

"Safe and effective amount" means an amount of a compound or composition sufficient to significantly induce a positive benefit, preferably a positive skin or feel benefit, including independently or in combinations the benefits disclosed herein, but low enough to avoid serious side effects, i.e., to provide a reasonable benefit to risk ratio, within the scope of sound judgment of the skilled artisan.

"Skin-care" means regulating and/or improving a skin condition. "Skin-care composition" means a composition that regulates and/or improves skin condition. A "skin moisturizing compositions" or a moisturizer means a composition that regulates and/or improves skin moisturization.

"The term dermatologically acceptable," as used herein, means that the compositions or components described are suitable for use in contact with human skin tissue.

"Topical application" means to apply or spread the compositions of the present invention onto the surface of the keratinous tissue.

Unless otherwise indicated, all numbers expressing quantities of ingredients, properties such as molecular weight, reaction conditions, and so forth as used in the specification and claims are to be understood as being modified in all instances by the term "about". Additionally, the disclosure of any ranges in the specification and claims are to be understood as including the range itself and also anything subsumed therein, as well as endpoints. All numeric ranges are inclusive of narrower ranges; delineated upper and lower range limits are interchangeable to create further ranges not explicitly delineated. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

Provided are methods for formulating skin moisturizing compositions based on the use of gene or biomarker panels for assessing the effects of test agents on skin moisturization. In the course of formulating skin moisturizing compositions for the skin, selection of the actives and other composition components may be guided by the application of the biomarkers that are shown herein to be reflective of skin health, particularly skin moisturization. Thus, in various embodiments, measurement of skin response to test agents provides information about the skin moisturizing effects of the test agents on skin. As further described herein, positive biomarker results correlate well with objective physical measurements of skin moisturization level. Thus the biomarker panel analysis described herein can be predictive of the ultimate benefit of an active in a skin care composition, and the methods incorporating the use of such biomarker panels allow for a relatively simple, efficient, and quick determination of the usefulness of a test agent for providing a moisturization benefit to skin.

In accordance with one aspect of the present invention, novel methods useful for the screening and generation of potential skin moisturizing actives for the treatment of dry skin are provided. The present inventors determined that beneficial effects of consumer personal care products, and particularly skin moisturizing agents, can be detected within the tissue and cells using one or more unique tissue and cellular biomarkers. In many instances, these changes have been demonstrated by the inventors to closely correlate with objective measurements of skin moisturization. Through genomic and bioinformatics analysis, the inventors identified and characterized various panels of biomarkers that demonstrate statistically significant moisturization changes within skin tissue in response to treatment with test agents. The use of the unique biomarker panels enables the efficient screening and identification of potential skin moisturizing actives as providing skin moisturizing benefits for use in any of a variety of formulations for consumer use.

Thus, the present inventors determined it is possible to derive unique biomarker panels for use in developing screening methods for identifying cosmetic test agents as effective for providing a moisturization benefit to human skin. These novel methods also allow for identification of new cosmetic agents that can be screened for their selective treatment of dry skin and for the specific targeting of the dry skin of particular populations. Examples of the dry skin of particular populations include subjects with inherently dry skin, subjects with inherently dry skin that is further exacerbated by seasonal effects (e.g. the winter season), subjects with inherently dry skin that is further exacerbated by treatment with a drying agent (e.g. a surfactant such as sodium lauryl sulphate (SLS)), subjects with inherently normal moisturized skin but with dry skin caused by seasonal effects, and subjects with inherently normal moisturized skin but with dry skin caused by treatment with a drying agent. As such, the invention provides methods uniquely suited for identifying skin moisturizing agents particularly suitable for desired treatment targets. Additionally, these methods are useful as they may serve as indicators of previously unidentified pathways associated with skin hydration, and thus can provide opportunities for identifying new classes of cosmetic agents.

Biomarker analysis can comprise quantitative and/or qualitative gene expression data measurements for a number of genes. The gene expression measurements may be compared to, e.g., a control sample, as described in more detail herein. Alternatively or in addition, gene expression measurements may be obtained from cells challenged in vitro. As described herein, a variety of biomarkers can be analyzed to assess the effects of one or more test agents on skin hydration. Accordingly, in various embodiments, biomarker panels may comprise one, two, or more different biomarkers. In some non-limiting examples, biomarkers include data related to the expression of at least one of REL, ITGB1, TGFBR2, YY1AP1, MAP3K, CASP3, TERT, MDM2, and LAMC2. Thus, non-limiting examples of biomarkers include levels of at least one of REL, ITGB1, TGFBR2, YY1AP1, MAP3K, CASP3, TERT, MDM2, and LAMC2. Further non-limiting examples of biomarkers of interest include data related to the expression of at least one of REL, ITGB1, TGFBR2, YY1AP1, MAP3K, CASP3, TERT, MDM2, and LAMC2. For example, biomarkers of interest can include the levels of messenger RNA ("mRNA") associated with the expression and/or regulation of at least one of REL, ITGB1, TGFBR2, YY1AP1, MAP3K, CASP3, TERT, MDM2, and LAMC2. Representative examples of biomarker analyses and various panels of biomarkers are described herein, as well as in the examples section. As described herein, a variety of agents were tested for their effects on skin moisturization, and biomarker panel testing results were analyzed for correlation with standard moisturization measurements. Standard moisturization measurements include, e.g., objective tools and techniques such as visual dry skin grading to measure the reduction of visual dryness and redness; trans-epidermal water loss (TEWL), skin hydration levels by a corneometer, elastic extension and elastic recovery by a Cutometer, and firmness, as compared to normal healthy control skin Gene expression for the development of the unique biomarker panels and for use in the screening methods for identifying cosmetic test agents as effective for providing a moisturization benefit to human skin may be detected and/or measured in a variety of ways. In some embodiments, the method for detecting gene expression comprises measuring the protein encoded by one or more genes of interest in a biomarker panel. Any suitable quantitative protein assay may be used herein. In certain embodiments, the method for detecting gene expression comprises measuring messenger ribonucleic acid ("mRNA") encoded by one or more genes of interest in a biomarker panel. Optionally, the method may include reverse transcribing mRNA encoded by one or more of the genes and measuring the corresponding complementary DNA ("cDNA"). Any suitable quantitative nucleic acid assay may be used herein. For example, conventional quantitative hybridization, Northern blot, and polymerase chain reaction procedures may be used for quantitatively measuring the amount of an mRNA transcript or cDNA in a biological sample. Optionally, the mRNA or cDNA may be amplified by polymerase chain reaction (PCR) prior to hybridization. The mRNA or cDNA sample is then examined by, e.g., hybridization with oligonucleotides specific for mRNAs or cDNAs encoded by one or more of the genes of the panel, optionally immobilized on a substrate (e.g., an array or microarray). Selection of one or more suitable probes specific for an mRNA or cDNA and selection of hybridization or PCR conditions are within the ordinary skill of those who work with nucleic acids. Binding of the biomarker nucleic acid to oligonucleotide probes specific for the biomarker(s) allows identification and quantification of the biomarker. Suitable examples of methods of quantifying gene expression are disclosed in U.S. Publication No. 2012/0283112; U.S. application Ser. Nos. 13/851,858, 13/851,864, 13/851,873, and 13/851,886; and U.S. Ser. No. 13/966,418, filed by Mills, et al., on Aug. 15, 2012.

For example, after exposure to the test agent and/or control, mRNA is extracted from the test cells and reference cells. The mRNA extracted from the cells may, optionally, be reverse transcribed to cDNA and marked with fluorescent dye(s) (e.g., red and green if a two color microarray analysis is to be performed). Alternatively, the cDNA samples may be prepped for a one color microarray analysis, and a plurality of replicates may be processed if desired. The cDNA samples may be co-hybridized to the microarray comprising a plurality of probes (e.g., tens, hundreds, or thousands of probes). In some embodiments, each probe on the microarray has a unique probe set identifier. The microarray is scanned by a scanner, which excites the dyes and measures the amount fluorescence. A computing device analyzes the raw images to determine the amount of cDNA present, which is representative of the expression levels of a gene.

The scanner may incorporate the functionality of the computing device. Typically, gene expression data collected by the system may include: i) up-regulation of gene expression (e.g., greater binding of the test material (e.g., cDNA) to probes compared to reference material (e.g., cDNA)), ii) down-regulation of gene expression (e.g., reduced binding of the test material (e.g., cDNA) to probes than the test material (e.g., cDNA)), iii) non-fluctuating gene expression (e.g., similar binding of the test material (e.g., cDNA) to the probes compared to the reference material (e.g., cDNA)), and iv) no detectable signal or noise. The up- and down-regulated genes may be referred to as "differentially expressed."

Microarrays and microarray analysis techniques are well known in the art, and it is contemplated that other microarray techniques may be used with the methods, devices, and systems of the invention. For example, any suitable commercial or non-commercial microarray technology and associated techniques may used, such as, but not limited to Affymetrix GeneChip™ technology and Illumina BeadChip™ technology. Furthermore, techniques for measuring and quantifying protein expression are well known in the art, and may be used with the methods, devices, and systems of the invention. One of skill in the art will appreciate that the invention is not limited to the methodology described above, and that other methods and techniques are also contemplated to be within its scope of the invention.

Gene expression measurement for can be done from full or partial human skin tissue samples or from simple cell types removed from such samples (such as through laser capture microdissection or physical cell or cell layer removal or other ways known in the art). Dermal and epidermal layers may be removed and analyzed separately or together. Any method suitable for obtaining epithelial tissue may be used, provided that the method obtains one or more of cellular debris, secretions from the epithelial tissue, and cells. Non-limiting examples of suitable obtaining techniques include, application of tape, rinsing by lavage method, biopsy, swabbing, scraping, blotting and combinations thereof. One particular suitable method of obtaining epithelial tissue is by application of tape, such as but not limited to, any type of medical tape. This technique is well known in the art and is relatively simple to implement. The technique involves application of a tape to the epithelial tissue, typically skin, which is then removed therefrom. The biomarker analytes obtained from the epithelial tissue and present on the tape are then removed from the tape in any fashion that preserves the biomarker analytes for suitable detection and measurement assays. Exemplary tapes include, but are not limited to: D-squame Tape®, and SEBUTAPE®, both of which are available from CuDerm Corporation, Dallas, Tex., USA; and Transpore® tape which is available from the 3M company, of Minnesota USA. However, whichever obtaining technique is used, it must be one where the biomarkers obtained are those present on the surface, and/or in the epithelial tissue and not include any of the underlying non-epithelial tissue, such as muscle. It will be appreciated that other methods of obtaining samples of epithelial tissue may be used, and can include not only tissue obtained from a subject, but also tissue that is cultured, such as live cells. For example, cell lines can be used to generate such gene expression profiles and resulting signatures, such as keratinocyte cell lines or fibroblast cell lines. Profiles can be generated from such individual cells, layers, or from multiple cells, layers, parts (or in whole) of the human skin tissue sample or samples. In accordance with some embodiments, the methods of the present involve obtaining samples of epithelial tissue to collect and analyze the biomarkers of interest.

A typical example of biomarker analysis for the development of the unique biomarker panels disclosed herein involves a method of measuring gene expression from test cells and comparing the gene expression measurements to reference gene expression measurements (e.g., taken from a control sample). The method may further comprise exposing test cells (e.g., keratinocytes and/or other skin cell or skin sample) to a test agent, such as a cosmetic test agent. The test agent may be dissolved in a suitable carrier such as dimethyl sulfoxide (DMSO). Optionally, reference gene expression measurements, which are typically taken from the same type of cell or from the same skin tissue sample as the test cells but which are only exposed to the carrier (i.e., no test agent), may be used as a control sample. In further aspects, reference gene expression measurements can be from control samples that include reference cells exposed to a positive control agent, such as known skin moisturizing actives. Non-limiting examples of such known skin moisturizing actives that can be used as a positive control agent include glycerin, zinc pyrithione (ZPT), monoolein, and olivem 1000. In other aspects, reference gene expression measurements can be from control samples that include reference cells exposed to a negative control agent, such skin drying agents as known in the art. In even further aspects, reference gene expression measurements can include the expression profile of the biomarker panel for a dry skin phenotype. Non-limiting examples of such expression profiles of biomarker panels for dry skin phenotypes that can serve as a negative control include: the expression profile of the biomarker panel specific for subjects with inherently dry skin; the expression profile of the biomarker panel specific for subjects with inherently dry skin that is further exacerbated by seasonal effects (e.g. during the winter season); the expression profile of the biomarker panel specific for subjects with inherently dry skin that is further exacerbated by treatment with a drying agent (e.g. a surfactant such as sodium lauryl sulphate (SLS)); the expression profile of the biomarker panel specific for subjects with inherently normal moisturized skin but with dry skin caused by seasonal effects (e.g. during the winter season); and the expression profile of the biomarker panel specific for subjects with inherently normal moisturized skin but with dry skin caused by treatment with a drying agent.

It will be appreciated that the methods herein are useful for benefiting users from a variety of populations. Accordingly, also provided are methods for developing personal skin moisturizing compositions and regimens of treatment for members of various populations. The methods involve testing proposed compositions or formulations on a plurality of individual subjects in a target population whereby the formulated personal care composition is optimized based on the measured biomarker responses in the target population. Target populations include subjects with inherently dry skin, subjects with inherently dry skin that is further exacerbated by seasonal effects (e.g. during the winter season), subjects with inherently dry skin that is further exacerbated by treatment with a drying agent (e.g. a surfactant such as sodium lauryl sulphate (SLS)), subjects with inherently normal moisturized skin but with dry skin caused by seasonal effects (e.g. during the winter season), and subjects with inherently normal moisturized skin but with dry skin caused by treatment with a drying agent. In some embodiments, the steps further include manufacturing the composition for the target population; and providing the composition in the delivery article. It will be appreciated that the method may be repeated for a different target population.

Biomarker panels and expression profiles of biomarker panels specific for certain populations may be derived by comparing gene expression data from a full thickness skin biopsy from skin of populations having the condition of interest and a control. These biomarker panels and expression profile of the biomarker panels can be specific for: subjects with inherently dry skin; subjects with inherently dry skin that is further exacerbated by seasonal effects (e.g. during the winter season); subjects with inherently dry skin that is further exacerbated by treatment with a drying agent (e.g. a surfactant such as sodium lauryl sulphate (SLS)); subjects with inherently normal moisturized skin but with dry skin caused by seasonal effects (e.g. during the winter season); and subjects with inherently normal moisturized skin but with dry skin caused by treatment with a drying agent. The examples, below, describe in greater detail non-limiting methods for deriving these biomarker panels and expression profiles of the biomarker panels.

Generally, for a biomarker panel and expression signature of a biomarker panel specific for subjects with inherently dry skin, biopsies may be taken from a plurality of subjects with inherently dry skin (e.g., as determined by a dry skin grade) and a plurality subjects with inherently normal moisturized skin (e.g., as determined by a dry skin grade). The subjects may vary in age, but one age range is between about 18 years of age and 65 years of age. A gene expression profiling analysis of the biopsy samples may be performed and one or more biomarker panels and expression signatures of the biomarker panels specific for subjects with inherently dry skin is derived from a statistical analysis of the results.

Generally, for a biomarker panel and expression signature of a biomarker panel specific for subjects with inherently dry skin that is further exacerbated by seasonal effects (e.g. during the winter season), biopsies may be taken from a plurality of subjects with inherently dry skin (e.g., as determined by a dry skin grade) in the winter season and a plurality subjects with inherently dry skin (e.g., as determined by a dry skin grade) in the summer season. The subjects may vary in age, but one age range is between about 18 years of age and 65 years of age. A gene expression profiling analysis of the biopsy samples may be performed and one or more biomarker panels and expression signatures of the biomarker panels specific for subjects with inherently dry skin that is further exacerbated by seasonal effects (e.g. during the winter season) is derived from a statistical analysis of the results.

Generally, for a biomarker panel and expression signature of a biomarker panel specific for subjects with inherently dry skin that is further exacerbated by treatment with a drying agent (e.g. a surfactant such as sodium lauryl sulphate (SLS)), biopsies may be taken from a plurality of subjects with inherently dry skin (e.g., as determined by a dry skin grade) that is treated with the drying agent and a plurality subjects with inherently dry skin (e.g., as determined by a dry skin grade) that is not treated with the drying agent. The subjects may vary in age, but one age range is between about 18 years of age and 65 years of age. A gene expression profiling analysis of the biopsy samples may be performed and one or more biomarker panels and expression signatures of the biomarker panels specific for subjects with inherently dry skin that is further exacerbated by treatment with a drying agent is derived from a statistical analysis of the results.

Generally, for a biomarker panel and expression signature of a biomarker panel specific for subjects with inherently normal moisturized skin but with dry skin caused by seasonal effects (e.g. during the winter season), biopsies may be taken from a plurality of subjects with inherently normal moisturized skin (e.g., as determined by a dry skin grade) in the winter season and a plurality subjects with inherently normal moisturized skin (e.g., as determined by a dry skin grade) in the summer season. The subjects may vary in age, but one age range is between about 18 years of age and 65 years of age. A gene expression profiling analysis of the biopsy samples may be performed and one or more biomarker panels and expression signatures of the biomarker panels specific for subjects with inherently normal moisturized skin but with dry skin caused by seasonal effects (e.g. during the winter season) is derived from a statistical analysis of the results.

Generally, for a biomarker panel and expression signature of a biomarker panel specific for subjects with inherently normal moisturized skin but with dry skin caused by treatment with a drying agent (e.g. a surfactant such as sodium lauryl sulphate (SLS)), biopsies may be taken from a plurality of subjects with inherently normal moisturized skin (e.g., as determined by a dry skin grade) that is treated with the drying agent and a plurality subjects with inherently normal moisturized skin (e.g., as determined by a dry skin grade) that is not treated with the drying agent. The subjects may vary in age, but one age range is between about 18 years of age and 65 years of age. A gene expression profiling analysis of the biopsy samples may be performed and one or more biomarker panels and expression signatures of the biomarker panels specific for subjects with inherently dry skin that is further exacerbated by treatment with a drying agent is derived from a statistical analysis of the results.

Biomarker panels and expression signature of biomarker panels specific for certain populations may also be derived from a gene expression analysis of skin cells treated with a positive control skin moisturizing agent, either in vivo or in vitro. As one illustrative example, microarray gene expression profile data where the positive control agent is a known skin moisturizing agent, such as glycerin, ZPT, monoolein, or olivem 1000, may be analyzed using the present invention. Thus, a list of genes strongly up-regulated and strongly down-regulated in response to challenge with a known skin moisturizing agent can be derived. Said list of genes (a proxy for skin moisturization) can be used in combination with the biomarker panels and expression signature of the biomarker panels specific for the human skin of specific populations of interest to provide unique and new biomarker panels and expression signatures of the biomarker panels which can serve as query panels to screen for skin moisturizing agents that will provide maximize efficacy and allow for the optimization of treatments. Furthermore, these unique biomarker panels and expression signatures of the biomarker panels may serve as indicators of previously unidentified pathways associated with DNA repair, and thus can provide opportunities for identifying new classes of cosmetic agents.

Non-limiting aspects and examples of various embodiments of skin screening methods will now be described. In certain embodiments, the methods allow for the screening of skin moisturizing agents. These novel methods also allow for identification of new skin moisturizing agents that can be screened for their specific targeting of the human skin of specific populations of interest. Examples of populations of interest include: subjects with inherently dry skin; subjects with inherently dry skin that is further exacerbated by seasonal effects (e.g. during the winter season); subjects with inherently dry skin that is further exacerbated by treatment with a drying agent (e.g. a surfactant such as sodium lauryl sulphate (SLS)); subjects with inherently normal moisturized skin but with dry skin caused by seasonal effects (e.g. during the winter season); and subjects with inherently normal moisturized skin but with dry skin caused by treatment with a drying agent. Thus, the invention provides methods uniquely suited for desired treatment targets. Additionally, these methods are particularly useful as they may serve as indicators of previously unidentified pathways associated with skin moisturization, and thus can provide opportunities for identifying new classes of cosmetic agents.

According to some embodiments of the invention, a screening method for identifying a cosmetic test agent as a skin moisturizing agent to human skin is provided. The method comprises: (a) contacting a skin tissue sample with a cosmetic test agent; (b) generating a transcriptional profile for the skin tissue sample, wherein the transcriptional profile comprises data related to the transcription of at least two genes selected from REL, ITGB1, TGFBR2, YY1AP1, MAP3K, CASP3, TERT, MDM2, LAMC2; and (c) comparing the transcriptional profile for the skin tissue sample to a control transcriptional profile. In certain embodiments, the control transcriptional profile is a positive control. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the method further comprises: (d) identifying the cosmetic test agent as a skin moisturizing agent for human skin when the transcriptional profile for the skin tissue sample and the control transcriptional profile are concordant. In such embodiments using a positive control, the cosmetic test agent is identified as a skin moisturizing agent if the transcriptional profile of the skin tissue sample and the control transcriptional profile correspond to a statistically significant upregulation in the transcription of REL, ITGB1, TGFBR2, CASP3, TERT, and/or LAMC2 and/or a statistically downregulation in the transcription of MAP3K, and/or MDM2. In some embodiments, these disclosed genes of interest may serve as to identify cosmetic agents that are skin moisturizing agents to the dry skin of subjects with inherently dry skin exacerbated by seasonal effects (e.g. during the winter season) or exacerbated by treatment with a drying agent, or to the dry skin of subjects with inherently normal moisturized skin but with dry skin caused by seasonal effects (e.g. during the winter season) or caused by treatment with a drying agent. Importantly, the disclosed unique gene expression signature may serve as indicators of previously unidentified pathways associated with dry skin repair, and thus can provide opportunities for identifying new classes of cosmetic agents.

In other embodiments, the control transcriptional profile is a negative control. A negative control can include, for example, a transcriptional profile of a skin tissue sample treated with a negative control agent, such as a drying agent. Additionally, a negative control can include the expression profile of the biomarker panel for a dry skin phenotype. Non-limiting examples of such expression profiles of biomarker panels for dry skin phenotypes that can serve as a negative control include: the expression profile of the biomarker panel specific for subjects with inherently dry skin; the expression profile of the biomarker panel specific for subjects with inherently dry skin that is further exacerbated by seasonal effects (e.g. during the winter season); the expression profile of the biomarker panel specific for subjects with inherently dry skin that is further exacerbated by treatment with a drying agent (e.g. a surfactant such as sodium lauryl sulphate (SLS)); the expression profile of the biomarker panel specific for subjects with inherently normal moisturized skin but with dry skin caused by seasonal effects (e.g. during the winter season); and the expression profile of the biomarker panel specific for subjects with inherently normal moisturized skin but with dry skin caused by treatment with a drying agent. In such embodiments, the method further comprises: (d) identifying the cosmetic test agent as a skin moisturizing agent for human skin when the transcriptional profile for the skin tissue sample and the control transcriptional profile are discordant. In such an embodiment using a negative control, the cosmetic test agent is identified as a skin moisturizing agent if the transcriptional profile of the skin tissue sample the control transcriptional profile corresponds to a statistically significant upregulation in the transcription of REL, ITGB1, TGFBR2, CASP3, TERT, and/or LAMC2 and/or a statistically downregulation in the transcription of MAP3K, and/or MDM2, as compared to transcriptional profile of the negative control. In some embodiments, these disclosed genes of interest may serve as to identify cosmetic agents that are skin moisturizing agents to the dry skin of subjects with inherently dry skin exacerbated by seasonal effects (e.g. during the winter season) or exacerbated by treatment with a drying agent, or to the dry skin of subjects with inherently normal moisturized skin but with dry skin caused by seasonal effects (e.g. during the winter season) or caused by treatment with a drying agent. Importantly, the disclosed unique gene expression signature may serve as indicators of previously unidentified pathways associated with dry skin repair, and thus can provide opportunities for identifying new classes of cosmetic agents.

According to another embodiment of the invention, a screening method for identifying a cosmetic test agent as a skin moisturizing agent to human skin is provided. The method comprises: (a) contacting a skin tissue sample with a cosmetic test agent; (b) generating a transcriptional profile for the skin tissue sample, wherein the transcriptional profile comprises data related to the transcription of at least two genes selected from REL, ITGB1, TGFBR2, YY1AP1, MAP3K, CASP3; and (c) comparing the transcriptional profile for the skin tissue sample to a control transcriptional profile. In certain embodiments, the control transcriptional profile is a positive control. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the method further comprises: (d) identifying the cosmetic test agent as a skin moisturizing agent for human skin when the transcriptional profile for the skin tissue sample and the control transcriptional profile are concordant. In such embodiments using a positive control, the cosmetic test agent is identified as a skin moisturizing agent if the transcriptional profile of the skin tissue sample and the control transcriptional profile correspond to a statistically significant upregulation in the transcription of REL, ITGB1, TGFBR2, and/or CASP3, and/or a statistically downregulation in the transcription of MAP3K. In some embodiments, these disclosed genes of interest may serve as to identify cosmetic agents that are skin moisturizing agents to the dry skin of subjects with inherently dry skin exacerbated by seasonal effects (e.g. during the winter season) or exacerbated by treatment with a drying agent, and to the dry skin of subjects with inherently normal moisturized skin but with dry skin caused by seasonal effects (e.g. during the winter season) or caused by treatment with a drying agent. Importantly, the disclosed unique gene expression signature may serve as indicators of previously unidentified pathways associated with dry skin repair, and thus can provide opportunities for identifying new classes of cosmetic agents.

In other embodiments, the control transcriptional profile is a negative control. A negative control can include, for example, a transcriptional profile of a skin tissue sample treated with a negative control agent, such as a drying agent. Additionally, a negative control can include the expression profile of the biomarker panel for a dry skin phenotype. Non-limiting examples of such expression profiles of biomarker panels for dry skin phenotypes that can serve as a negative control include: the expression profile of the biomarker panel specific for subjects with inherently dry skin; the expression profile of the biomarker panel specific for subjects with inherently dry skin that is further exacerbated by seasonal effects (e.g. during the winter season); the expression profile of the biomarker panel specific for subjects with inherently dry skin that is further exacerbated by treatment with a drying agent (e.g. a surfactant such as sodium lauryl sulphate (SLS)); the expression profile of the biomarker panel specific for subjects with inherently normal moisturized skin but with dry skin caused by seasonal effects (e.g. during the winter season); and the expression profile of the biomarker panel specific for subjects with inherently normal moisturized skin but with dry skin caused by treatment with a drying agent. In such embodiments, the method further comprises: (d) identifying the cosmetic test agent as a skin moisturizing agent for human skin when the transcriptional profile for the skin tissue sample and the control transcriptional profile are discordant. In such embodiments using a negative control, the cosmetic test agent is identified as a skin moisturizing agent if the transcriptional profile of the skin tissue sample the control transcriptional profile corresponds to a statistically significant upregulation in the transcription of REL, ITGB1, TGFBR2, and/or CASP3, and/or a statistically downregulation in the transcription of MAP3K, as compared to transcriptional profile of the negative control. In some embodiments, these disclosed genes of interest may serve as to identify cosmetic agents that are skin moisturizing agents to the dry skin of subjects with inherently dry skin exacerbated by seasonal effects (e.g. during the winter season) or exacerbated by treatment with a drying agent, and to the dry skin of subjects with inherently normal moisturized skin but with dry skin caused by seasonal effects (e.g. during the winter season) or caused by treatment with a drying agent. Importantly, the disclosed unique gene expression signature may serve as indicators of previously unidentified pathways associated with dry skin repair, and thus can provide opportunities for identifying new classes of cosmetic agents.

Another embodiment of the invention is directed to a screening method for identifying a cosmetic test agent as a skin moisturizing agent to human skin is provided. The method comprises: (a) contacting a skin tissue sample with a cosmetic test agent; (b) generating a transcriptional profile for the skin tissue sample, wherein the transcriptional profile comprises data related to the transcription of at least two genes selected from TERT, MAP3K, LAMC2, MDM2; and (c) comparing the transcriptional profile for the skin tissue sample to a control transcriptional profile. In certain embodiments, the control transcriptional profile is a positive control. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the method further comprises: (d) identifying the cosmetic test agent as a skin moisturizing agent for human skin when the transcriptional profile for the skin tissue sample and the control transcriptional profile are concordant. In such embodiments using a positive control, the cosmetic test agent is identified as a skin moisturizing agent if the transcriptional profile of the skin tissue sample and the control transcriptional profile correspond to a statistically significant upregulation in the transcription of TERT, and/or LAMC2 and/or a statistically downregulation in the transcription of MAP3K, and/or MDM2. These disclosed genes of interest may serve as a set to identify cosmetic agents that are skin moisturizing agents to the dry skin of subjects with inherently dry skin further exacerbated by seasonal effects (e.g. during the winter season) or exacerbated by treatment with a drying agent. Importantly, the disclosed unique gene expression signature may serve as indicators of previously unidentified pathways associated with dry skin repair, and thus can provide opportunities for identifying new classes of cosmetic agents.

In other embodiments, the control transcriptional profile is a negative control. A negative control can include, for example, a transcriptional profile of a skin tissue sample treated with a negative control agent, such as a drying agent. Additionally, a negative control can include the expression profile of the biomarker panel for a dry skin phenotype including the expression profile of the biomarker panel specific for subjects with inherently dry skin that is further exacerbated by seasonal effects (e.g. during the winter season); and the expression profile of the biomarker panel specific for subjects with inherently dry skin that is further exacerbated by treatment with a drying agent (e.g. a surfactant such as sodium lauryl sulphate (SLS)). In such embodiments, the method further comprises: (d) identifying the cosmetic test agent as a skin moisturizing agent for human skin when the transcriptional profile for the skin tissue sample and the control transcriptional profile are discordant. In such embodiments using a negative control, the cosmetic test agent is identified as a skin moisturizing agent if the transcriptional profile of the skin tissue sample the control transcriptional profile corresponds to a statistically significant upregulation in the transcription of TERT, and/or LAMC2 and/or a statistically downregulation in the transcription of MAP3K, and/or MDM2, as compared to transcriptional profile of the negative control. These disclosed genes of interest may serve as a set to identify cosmetic agents that are skin moisturizing agents to the dry skin of subjects with inherently dry skin further exacerbated by seasonal effects (e.g. during the winter season) or exacerbated by treatment with a drying agent. Importantly, the disclosed unique gene expression signature may serve as indicators of previously unidentified pathways associated with dry skin repair, and thus can provide opportunities for identifying new classes of cosmetic agents.

An additional embodiment of the invention is directed to a screening method for identifying a cosmetic test agent as a skin moisturizing agent to human skin is provided. The method comprises: (a) contacting a skin tissue sample with a cosmetic test agent; (b) generating a transcriptional profile for the skin tissue sample, wherein the transcriptional profile comprises data related to the transcription of at least two genes selected from REL, ITGB1, TGFBR2, TERT, MAP3K, LAMC2; and (c) comparing the transcriptional profile for the skin tissue sample to a control transcriptional profile. In certain embodiments, the control transcriptional profile is a positive control. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the method further comprises: (d) identifying the cosmetic test agent as a skin moisturizing agent for human skin when the transcriptional profile for the skin tissue sample and the control transcriptional profile are concordant. In such embodiments using a positive control, the cosmetic test agent is identified as a skin moisturizing agent if the transcriptional profile of the skin tissue sample and the control transcriptional profile correspond to a statistically significant upregulation in the transcription of REL, ITGB1, TGFBR2, TERT and/or LAMC2, and/or a statistically downregulation in the transcription of MAP3K. These disclosed genes of interest may serve as a set to identify cosmetic agents that are skin moisturizing agents to the dry skin of subjects with inherently dry skin further exacerbated by treatment with a drying agent or to the dry skin of subjects with inherently normal moisturized skin but with dry skin caused treatment with a drying agent. Importantly, the disclosed unique gene expression signature may serve as indicators of previously unidentified pathways associated with dry skin repair, and thus can provide opportunities for identifying new classes of cosmetic agents.

In other embodiments, the control transcriptional profile is a negative control. A negative control can include, for example, a transcriptional profile of a skin tissue sample treated with a negative control agent, such as a drying agent. Additionally, a negative control can include the expression profile of the biomarker panel for a dry skin phenotype including the expression profile of the biomarker panel specific for subjects with inherently dry skin that is further exacerbated by treatment with a drying agent (e.g. a surfactant such as sodium lauryl sulphate (SLS)) and the expression profile of the biomarker panel specific for subjects with inherently normal moisturized skin but with dry skin caused by treatment with a drying agent. In such embodiments, the method further comprises: (d) identifying the cosmetic test agent as a skin moisturizing agent for human skin when the transcriptional profile for the skin tissue sample and the control transcriptional profile are discordant. In such embodiments using a negative control, the cosmetic test agent is identified as a skin moisturizing agent if the transcriptional profile of the skin tissue sample the control transcriptional profile corresponds to a statistically significant upregulation in the transcription of REL, ITGB1, TGFBR2, TERT, and/or LAMC2 and/or a statistically downregulation in the transcription of MAP3K, as compared to transcriptional profile of the negative control. These disclosed genes of interest may serve as a set to identify cosmetic agents that are skin moisturizing agents to the dry skin of subjects with inherently dry skin further exacerbated by treatment with a drying agent or to the dry skin of subjects with inherently normal moisturized skin but with dry skin caused treatment with a drying agent. Importantly, the disclosed unique gene expression signature may serve as indicators of previously unidentified pathways associated with dry skin repair, and thus can provide opportunities for identifying new classes of cosmetic agents.

A further embodiment of the invention is directed to a screening method for identifying a cosmetic test agent as a skin moisturizing agent to human skin is provided. The method comprises: (a) contacting a skin tissue sample with a cosmetic test agent; (b) generating a transcriptional profile for the skin tissue sample, wherein the transcriptional profile comprises data related to the transcription of at least two genes selected from REL, ITGB1, TGFBR2; and (c) comparing the transcriptional profile for the skin tissue sample to a control transcriptional profile. In certain embodiments, the control transcriptional profile is a positive control. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the method further comprises: (d) identifying the cosmetic test agent as a skin moisturizing agent for human skin when the transcriptional profile for the skin tissue sample and the control transcriptional profile are concordant. In such embodiments using a positive control, the cosmetic test agent is identified as a skin moisturizing agent if the transcriptional profile of the skin tissue sample and the control transcriptional profile correspond to a statistically significant upregulation in the transcription of REL, ITGB1, and/or TGFBR2. These disclosed genes of interest may serve as a set to identify cosmetic agents that are skin moisturizing agents to the dry skin of subjects with inherently dry skin further exacerbated by treatment with a drying agent and to the dry skin of subjects with inherently normal moisturized skin but with dry skin caused treatment with a drying agent. Importantly, the disclosed unique gene expression signature may serve as indicators of previously unidentified pathways associated with dry skin repair, and thus can provide opportunities for identifying new classes of cosmetic agents.

In other embodiments, the control transcriptional profile is a negative control. A negative control can include, for example, a transcriptional profile of a skin tissue sample treated with a negative control agent, such as a drying agent. Additionally, a negative control can include the expression profile of the biomarker panel for a dry skin phenotype including the expression profile of the biomarker panel specific for subjects with inherently dry skin that is further exacerbated by treatment with a drying agent (e.g. a surfactant such as sodium lauryl sulphate (SLS)) and the expression profile of the biomarker panel specific for subjects with inherently normal moisturized skin but with dry skin caused by treatment with a drying agent. In such embodiments, the method further comprises: (d) identifying the cosmetic test agent as a skin moisturizing agent for human skin when the transcriptional profile for the skin tissue sample and the control transcriptional profile are discordant. In such an embodiment using a negative control, the cosmetic test agent is identified as a skin moisturizing agent if the transcriptional profile of the skin tissue sample the control transcriptional profile corresponds to a statistically significant upregulation in the transcription of REL, ITGB1, and/or TGFBR2 as compared to transcriptional profile of the negative control. These disclosed genes of interest may serve as a set to identify cosmetic agents that are skin moisturizing agents to the dry skin of subjects with inherently dry skin further exacerbated by treatment with a drying agent and to the dry skin of subjects with inherently normal moisturized skin but with dry skin caused treatment with a drying agent. Importantly, the disclosed unique gene expression signature may serve as indicators of previously unidentified pathways associated with dry skin repair, and thus can provide opportunities for identifying new classes of cosmetic agents.

Another embodiment of the invention is directed to a screening method for identifying a cosmetic test agent as a skin moisturizing agent to human skin is provided. The method comprises: (a) contacting a skin tissue sample with a cosmetic test agent; (b) generating a transcriptional profile for the skin tissue sample, wherein the transcriptional profile comprises data related to the transcription of at least two genes selected from TERT, MAP3K, LAMC2; and (c) comparing the transcriptional profile for the skin tissue sample to a control transcriptional profile. In certain embodiments, the control transcriptional profile is a positive control. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the method further comprises: (d) identifying the cosmetic test agent as a skin moisturizing agent for human skin when the transcriptional profile for the skin tissue sample and the control transcriptional profile are concordant. In such embodiments using a positive control, the cosmetic test agent is identified as a skin moisturizing agent if the transcriptional profile of the skin tissue sample and the control transcriptional profile correspond to a statistically significant upregulation in the transcription of TERT and/or LAMC2 and/or a statistically downregulation in the transcription of MAP3K. These disclosed genes of interest may serve as a set to identify cosmetic agents that are skin moisturizing agents to the dry skin of subjects with inherently dry skin further exacerbated by treatment with a drying agent. Importantly, the disclosed unique gene expression signature may serve as indicators of previously unidentified pathways associated with dry skin repair, and thus can provide opportunities for identifying new classes of cosmetic agents.

In other embodiments, the control transcriptional profile is a negative control. A negative control can include, for example, a transcriptional profile of a skin tissue sample treated with a negative control agent, such as a drying agent. Additionally, a negative control can include the expression profile of the biomarker panel for a dry skin phenotype including the expression profile of the biomarker panel specific for subjects with inherently dry skin that is further exacerbated by treatment with a drying agent (e.g. a surfactant such as sodium lauryl sulphate (SLS)). In such embodiments, the method further comprises: (d) identifying the cosmetic test agent as a skin moisturizing agent for human skin when the transcriptional profile for the skin tissue sample and the control transcriptional profile are discordant. In such embodiments using a negative control, the cosmetic test agent is identified as a skin moisturizing agent if the transcriptional profile of the skin tissue sample the control transcriptional profile corresponds to a statistically significant upregulation in the transcription of TERT, and/or LAMC2 and/or a statistically downregulation in the transcription of MAP3K, as compared to transcriptional profile of the negative control. These disclosed genes of interest may serve as a set to identify cosmetic agents that are skin moisturizing agents to the dry skin of subjects with inherently dry skin further exacerbated by treatment with a drying agent. Importantly, the disclosed unique gene expression signature may serve as indicators of previously unidentified pathways associated with dry skin repair, and thus can provide opportunities for identifying new classes of cosmetic agents.

An additional embodiment of the invention is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profile comprises data related to the transcription of at least two genes selected from TERT, MDM2, LAMC2; and (c) comparing the transcriptional profile for the skin tissue sample to a control transcriptional profile. In certain embodiments, the control transcriptional profile is a positive control. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the method further comprises: (d) identifying the cosmetic test agent as a skin moisturizing agent for human skin when the transcriptional profile for the skin tissue sample and the control transcriptional profile are concordant. In such embodiments using a positive control, the cosmetic test agent is identified as a skin moisturizing agent if the transcriptional profile of the skin tissue sample and the control transcriptional profile correspond to a statistically significant upregulation in the transcription of TERT, and/or LAMC2 and/or a statistically downregulation in the transcription of MDM2. These disclosed genes of interest may serve as a set to identify cosmetic agents that are skin moisturizing agents to the dry skin of subjects with inherently dry skin further exacerbated seasonal effects (e.g. during the winter season). Importantly, the disclosed unique gene expression signature may serve as indicators of previously unidentified pathways associated with dry skin repair, and thus can provide opportunities for identifying new classes of cosmetic agents.

In other embodiments, the control transcriptional profile is a negative control. A negative control can include the expression profile of the biomarker panel for a dry skin phenotype including the expression profile of the biomarker panel specific for subjects with inherently dry skin that is further exacerbated by seasonal effects (e.g. during the winter season). In such embodiments, the method further comprises: (d) identifying the cosmetic test agent as a skin moisturizing agent for human skin when the transcriptional profile for the skin tissue sample and the control transcriptional profile are discordant. In such embodiments using a negative control, the cosmetic test agent is identified as a skin moisturizing agent if the transcriptional profile of the skin tissue sample the control transcriptional profile corresponds to a statistically significant upregulation in the transcription of TERT, and/or LAMC2 and/or a statistically downregulation in the transcription of MDM2, as compared to transcriptional profile of the negative control. These disclosed genes of interest may serve as a set to identify cosmetic agents that are skin moisturizing agents to the dry skin of subjects with inherently dry skin further exacerbated seasonal effects (e.g. during the winter season). Importantly, the disclosed unique gene expression signature may serve as indicators of previously unidentified pathways associated with dry skin repair, and thus can provide opportunities for identifying new classes of cosmetic agents.

A further embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from REL, ITGB1, TGFBR2, MAP3K, CASP3, TERT, MDM2, LAMC2; (c) comparing the transcriptional profile for the skin tissue sample to a positive control transcriptional profile; and (d) identifying the cosmetic test agent as a skin moisturizing agent for human skin when the transcriptional profile for the skin tissue sample and the positive control transcriptional profile are concordant. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the cosmetic test agent is identified as a skin moisturizing agent if the transcriptional profile of the skin tissue sample and the positive control transcriptional profile correspond to a statistically significant upregulation in the transcription of REL, ITGB1, TGFBR2, CASP3, TERT, and/or LAMC2 and/or a statistically downregulation in the transcription of MAP3K, and/or MDM2. In some embodiments, the disclosed genes of interest may serve as to identify cosmetic agents that are skin moisturizing agents to the dry skin of subjects with inherently dry skin exacerbated by seasonal effects (e.g. during the winter season) or exacerbated by treatment with a drying agent, or to the dry skin of subjects with inherently normal moisturized skin but with dry skin caused by seasonal effects (e.g. during the winter season) or caused by treatment with a drying agent. In certain embodiments, the positive control agent can be glycerin, ZPT, monoolein, or olivem 1000. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least two genes selected from REL, TERT, MDM2, LAMC2. In such an embodiment, the positive control is glycerin. In such an embodiment, the cosmetic test agent is identified as a skin moisturizing agent if the transcriptional profile of the skin tissue sample and the positive control transcriptional profile correspond to a statistically significant upregulation in the transcription of REL, TERT, and/or LAMC2 and/or a statistically downregulation in the transcription of MDM2. In other particular embodiments, the transcriptional profile comprises data related to transcription of at least two genes selected from TERT, MDM2, CASP3. In such an embodiment, the positive control is ZPT. In such an embodiment, the cosmetic test agent is identified as a skin moisturizing agent if the transcriptional profile of the skin tissue sample and the positive control transcriptional profile correspond to a statistically significant upregulation in the transcription of CASP3, and/or TERT, and/or a statistically downregulation in the transcription of MDM2. In further particular embodiments, the transcriptional profile comprises data related to transcription of at least two genes selected from ITGB1, TGFBR2, MDM2. In such embodiments, the cosmetic test agent is identified as a skin moisturizing agent if the transcriptional profile of the skin tissue sample and the positive control transcriptional profile correspond to a statistically significant upregulation in the transcription of ITGB1 and/or TGFBR2, and/or a statistically downregulation in the transcription of MDM2. In such an embodiment, the positive control is monoolein. In even further embodiments, the transcriptional profile comprises data related to transcription of at least two genes selected from REL, TGFBR2, MAP3K, CASP3. In such an embodiment, the positive control is olivem 1000. In such embodiments, the cosmetic test agent is identified as a skin moisturizing agent if the transcriptional profile of the skin tissue sample and the control transcriptional profile correspond to a statistically significant upregulation in the transcription of REL, TGFBR2, and/or CASP3, and/or a statistically downregulation in the transcription of MAP3K.

An additional embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from REL, ITGB1, TGFBR2, MAP3K, CASP3; (c) comparing the transcriptional profile for the skin tissue sample to a positive control transcriptional profile; and (d) identifying the cosmetic test agent as a skin moisturizing agent for human skin when the transcriptional profile for the skin tissue sample and the positive control transcriptional profile are concordant. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiment, the cosmetic test agent can be identified as a skin moisturizing agent if the transcriptional profile of the skin tissue sample and the positive control transcriptional profile correspond to a statistically significant upregulation in the transcription of REL, ITGB1, TGFBR2, and/or CASP3, and/or a statistically downregulation in the transcription of MAP3K. In some embodiments, the disclosed genes of interest may serve to identify cosmetic agents that are skin moisturizing agents to the dry skin of subjects with inherently dry skin exacerbated by seasonal effects (e.g. during the winter season) or exacerbated by treatment with a drying agent, and to the dry skin of subjects with inherently normal moisturized skin but with dry skin caused by seasonal effects (e.g. during the winter season) or caused by treatment with a drying agent. In certain embodiments, the positive control can be glycerin, ZPT, monoolein, or olivem 1000. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least two genes selected from REL, MAP3K. In such an embodiment, the positive control is glycerin. In such embodiments, the cosmetic test agent can be identified as a skin moisturizing agent if the transcriptional profile of the skin tissue sample and the positive control transcriptional profile correspond to a statistically significant upregulation in the transcription of REL and/or a statistically downregulation in the transcription of MAP3K. In other particular embodiments, the transcriptional profile comprises data related to transcription of at least CASP3. In such an embodiment, the positive control is ZPT. In such embodiments, the cosmetic test agent can be identified as a skin moisturizing agent if the transcriptional profile of the skin tissue sample and the positive control transcriptional profile correspond to a statistically significant upregulation in the transcription of CASP3. In further particular embodiments, the transcriptional profile comprises data related to transcription of at least ITGB1, TGFBR2. In such an embodiment, the positive control is monoolein. In such embodiments, the cosmetic test agent can identified as a skin moisturizing agent if the transcriptional profile of the skin tissue sample and the positive control transcriptional profile correspond to a statistically significant upregulation in the transcription of ITGB1 and/or TGFBR2. In even further embodiments, the transcriptional profile comprises data related to transcription of at least two genes selected from REL, TGFBR2, MAP3K, CASP3. In such an embodiment, the positive control is olivem 1000. In such embodiments, the cosmetic test agent can identified as a skin moisturizing agent if the transcriptional profile of the skin tissue sample and the control transcriptional profile correspond to a statistically significant upregulation in the transcription of REL, TGFBR2, and/or CASP3, and/or a statistically downregulation in the transcription of MAP3K.

A further embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from TERT, MDM2, MAP3K, LAMC2; (c) comparing the transcriptional profile for the skin tissue sample to a positive control transcriptional profile; and (d) identifying the cosmetic test agent as a skin moisturizing agent for human skin when the transcriptional profile for the skin tissue sample and the control transcriptional profile are concordant. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the cosmetic test agent is identified as a skin moisturizing agent if the transcriptional profile of the skin tissue sample and the control transcriptional profile correspond to a statistically significant upregulation in the transcription of TERT, and/or LAMC2 and/or a statistically downregulation in the transcription of MAP3K, and/or MDM2. The disclosed genes of interest may serve as a biomarker panel to identify cosmetic agents that are skin moisturizing agents to the dry skin of subjects with inherently dry skin further exacerbated by seasonal effects (e.g. during the winter season) or exacerbated by treatment with a drying agent. In certain embodiments, the positive control can be glycerin, ZPT, monoolein, or olivem 1000. In particular embodiments, the positive control is glycerin. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least TERT, MDM2. In such an embodiment, the positive control is ZPT. In such embodiments, the cosmetic test agent is identified as a skin moisturizing agent if the transcriptional profile of the skin tissue sample and the positive control transcriptional profile correspond to a statistically significant upregulation in the transcription of TERT and/or a statistically downregulation in the transcription of MDM2. In further particular embodiments, the transcriptional profile comprises data related to transcription of at least MDM2. In such embodiments, the cosmetic test agent is identified as a skin moisturizing agent if the transcriptional profile of the skin tissue sample and the positive control transcriptional profile correspond to a statistically downregulation in the transcription of MDM2. In such an embodiment, the positive control is monoolein. In even further embodiments, the transcriptional profile comprises data related to transcription of at least MAP3K. In such an embodiment, the positive control is olivem 1000. In such embodiments, the cosmetic test agent is identified as a skin moisturizing agent if the transcriptional profile of the skin tissue sample and the positive control transcriptional profile correspond to a statistically downregulation in the transcription of MAP3K.

Another embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from REL, ITGB1, TGFBR2, TERT, MAP3K, LAMC2; (c) comparing the transcriptional profile for the skin tissue sample to a positive control transcriptional profile; and (d) identifying the cosmetic test agent as a skin moisturizing agent for human skin when the transcriptional profile for the skin tissue sample and the positive control transcriptional profile are concordant. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the cosmetic test agent is identified as a skin moisturizing agent if the transcriptional profile of the skin tissue sample and the positive control transcriptional profile correspond to a statistically significant upregulation in the transcription of REL, ITGB1, TGFBR2, TERT, and/or LAMC2 and/or a statistically downregulation in the transcription of MAP3K, and/or MDM2. The disclosed genes of interest may serve as a set to identify cosmetic agents that are skin moisturizing agents to the dry skin of subjects with inherently dry skin further exacerbated by treatment with a drying agent or to the dry skin of subjects with inherently normal moisturized skin but with dry skin caused treatment with a drying agent. In certain embodiments, the positive control can be glycerin, ZPT, monoolein, or olivem 1000. In particular embodiments, the positive control is glycerin. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least two genes selected from REL, TERT, MAP3K, LAMC2. In such an embodiment, the positive control is glycerin. In such embodiments, the cosmetic test agent is identified as a skin moisturizing agent if the transcriptional profile of the skin tissue sample and the positive control transcriptional profile correspond to a statistically significant upregulation in the transcription of REL, TERT, and/or LAMC2, and/or a statistically downregulation in the transcription of MAP3K. In other particular embodiments, the transcriptional profile comprises data related to transcription of at least TERT. In such an embodiment, the positive control is ZPT. In such embodiments, the cosmetic test agent is identified as a skin moisturizing agent if the transcriptional profile of the skin tissue sample and the positive control transcriptional profile correspond to a statistically significant upregulation in the transcription of TERT. In further particular embodiments, the transcriptional profile comprises data related to transcription of at least ITGB1, TERT. In such an embodiment, the positive control is monoolein. In such embodiments, the cosmetic test agent is identified as a skin moisturizing agent if the transcriptional profile of the skin tissue sample and the positive control transcriptional profile correspond to a statistically significant upregulation in the transcription of ITGB1, and/or TERT. In even further embodiments, the transcriptional profile comprises data related to transcription of at least two genes selected from REL, TGFBR2, MAP3K. In such an embodiment, the positive control is olivem 1000. In such embodiments, the cosmetic test agent is identified as a skin moisturizing agent if the transcriptional profile of the skin tissue sample and the positive control transcriptional profile correspond to a statistically significant upregulation in the transcription of REL and/or TGFBR2 and/or a statistically downregulation in the transcription of MAP3K.

An additional embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from REL, ITGB1, TGFBR2; (c) comparing the transcriptional profile for the skin tissue sample to a positive control transcriptional profile; and (d) identifying the cosmetic test agent as a skin moisturizing agent for human skin when the transcriptional profile for the skin tissue sample and the positive control transcriptional profile are concordant. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the cosmetic test agent is identified as a skin moisturizing agent if the transcriptional profile of the skin tissue sample and the positive control transcriptional profile correspond to a statistically significant upregulation in the transcription of REL, ITGB1, and/or TGFBR2. The disclosed genes of interest may serve as a set to identify cosmetic agents that are skin moisturizing agents to the dry skin of subjects with inherently dry skin further exacerbated by treatment with a drying agent and to the dry skin of subjects with inherently normal moisturized skin but with dry skin caused treatment with a drying agent. In certain embodiments, the positive control can be glycerin, monoolein, or olivem 1000. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least REL. In such an embodiment, the positive control is glycerin. In such embodiments, the cosmetic test agent is identified as a skin moisturizing agent if the transcriptional profile of the skin tissue sample and the positive control transcriptional profile correspond to a statistically significant upregulation in the transcription of REL. In further particular embodiments, the transcriptional profile comprises data related to transcription of at least ITGB1, TGFBR2. In such embodiments, the cosmetic test agent is identified as a skin moisturizing agent if the transcriptional profile of the skin tissue sample and the positive control transcriptional profile correspond to a statistically significant upregulation in the transcription of ITGB1 and/or TGFBR2. In such an embodiment, the positive control is monoolein. In even further embodiments, the transcriptional profile comprises data related to transcription of at least REL, TGFBR2. In such an embodiment, the positive control is olivem 1000. In such embodiments, the cosmetic test agent is identified as a skin moisturizing agent if the transcriptional profile of the skin tissue sample and the positive control transcriptional profile correspond to a statistically significant upregulation in the transcription of REL and/or TGFBR2.

A further embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from TERT, MAP3K, LAMC2; (c) comparing the transcriptional profile for the skin tissue sample to a positive control transcriptional profile; and (d) identifying the cosmetic test agent as a skin moisturizing agent for human skin when the transcriptional profile for the skin tissue sample and the positive control transcriptional profile are concordant. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the cosmetic test agent is identified as a skin moisturizing agent if the transcriptional profile of the skin tissue sample and the positive control transcriptional profile correspond to a statistically significant upregulation in the transcription of TERT, and/or LAMC2 and/or a statistically downregulation in the transcription of MAP3K. The disclosed genes of interest may serve as a set to identify cosmetic agents that are skin moisturizing agents to the dry skin of subjects with inherently dry skin further exacerbated by treatment with a drying agent. In certain embodiments, the positive control can be glycerin, ZPT, or olivem 1000. In particular embodiments, the positive control is glycerin. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least TERT. In such an embodiment, the positive control is ZPT. In such embodiments, the cosmetic test agent is identified as a skin moisturizing agent if the transcriptional profile of the skin tissue sample and the positive control transcriptional profile correspond to a statistically significant upregulation in the transcription of TERT. In further particular embodiments, the transcriptional profile comprises data related to transcription of at least MAP3K. In such an embodiment, the positive control is olivem 1000. In such embodiments, the cosmetic test agent is identified as a skin moisturizing agent if the transcriptional profile of the skin tissue sample and the positive control transcriptional profile correspond to a statistically downregulation in the transcription of MAP3K.

Another embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from REL, ITGB1, TGFBR2, MAP3K, CASP3, TERT, MDM2, LAMC2; (c) comparing the transcriptional profile for the skin tissue sample to a positive control transcriptional profile; and (d) identifying the cosmetic test agent as a skin moisturizing agent for human skin when the transcriptional profile for the skin tissue sample and the positive control transcriptional profile are concordant. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the cosmetic test agent is identified as a skin moisturizing agent if the transcriptional profile of the skin tissue sample and the positive control transcriptional profile correspond to a statistically significant upregulation in the transcription of REL, ITGB1, TGFBR2, CASP3, TERT, and/or LAMC2 and/or a statistically downregulation in the transcription of MAP3K, and/or MDM2. In some embodiments, the disclosed genes of interest may serve as to identify cosmetic agents that are skin moisturizing agents to the dry skin of subjects with inherently dry skin exacerbated by seasonal effects (e.g. during the winter season), or to the dry skin of subjects with inherently normal moisturized skin but with dry skin caused by seasonal effects (e.g. during the winter season). In certain embodiments, the positive control can be glycerin, ZPT, monoolein, or olivem 1000. In particular embodiments, the positive control is glycerin. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least two genes selected from REL, TERT, MDM2, MAP3K, LAMC2. In such an embodiment, the positive control is glycerin. In such embodiments, the cosmetic test agent is identified as a skin moisturizing agent if the transcriptional profile of the skin tissue sample and the positive control transcriptional profile correspond to a statistically significant upregulation in the transcription of REL, TERT, and/or LAMC2 and/or a statistically downregulation in the transcription of MAP3K, and/or MDM2. In other particular embodiments, the transcriptional profile comprises data related to transcription of at least two genes selected from TERT, MDM2, CASP3. In such an embodiment, the positive control is ZPT. In such embodiments, the cosmetic test agent is identified as a skin moisturizing agent if the transcriptional profile of the skin tissue sample and the positive control transcriptional profile correspond to a statistically significant upregulation in the transcription of CASP3 and/or TERT and/or a statistically downregulation in the transcription of MDM2. In further particular embodiments, the transcriptional profile comprises data related to transcription of at least ITGB1, TGFBR2, MDM2. In such an embodiment, the positive control is monoolein. In such embodiments, the cosmetic test agent is identified as a skin moisturizing agent if the transcriptional profile of the skin tissue sample and the positive control transcriptional profile correspond to a statistically significant upregulation in the transcription of ITGB1 and/or TGFBR2, and/or a statistically downregulation in the transcription of MDM2. In even further embodiments, the transcriptional profile comprises data related to transcription of at least two genes selected from REL, TGFBR2, MAP3K, CASP3. In such an embodiment, the positive control is olivem 1000. In such embodiments, the cosmetic test agent is identified as a skin moisturizing agent if the transcriptional profile of the skin tissue sample and the positive control transcriptional profile correspond to a statistically significant upregulation in the transcription of REL, TGFBR2, and/or CASP3, and/or a statistically downregulation in the transcription of MAP3K.

A further embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from REL, ITGB1, TGFBR2, MAP3K, CASP3; (c) comparing the transcriptional profile for the skin tissue sample to a positive control transcriptional profile; and (d) identifying the cosmetic test agent as a skin moisturizing agent for human skin when the transcriptional profile for the skin tissue sample and the positive control transcriptional profile are concordant. A positive control can include, for example, a transcriptional profile of a skin tissue sample treated with a positive control agent such as glycerin, zinc pyrithione (ZPT), monoolein, and olive 1000. Thus, in some embodiments, the positive control transcriptional profile is a second skin tissue sample contacted with a positive control agent. In such embodiments, the cosmetic test agent is identified as a skin moisturizing agent if the transcriptional profile of the skin tissue sample and the positive control transcriptional profile correspond to a statistically significant upregulation in the transcription of REL, ITGB1, TGFBR2, and/or CASP3, and/or a statistically downregulation in the transcription of MAP3K. In some embodiments, the disclosed genes of interest may serve as to identify cosmetic agents that are skin moisturizing agents to the dry skin of subjects with inherently dry skin exacerbated by seasonal effects (e.g. during the winter season), and to the dry skin of subjects with inherently normal moisturized skin but with dry skin caused by seasonal effects (e.g. during the winter season). In certain embodiments, the positive control can be glycerin, ZPT, monoolein, or olivem 1000. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least REL, MAP3K. In such an embodiment, the positive control is glycerin. In such embodiments, the cosmetic test agent is identified as a skin moisturizing agent if the transcriptional profile of the skin tissue sample and the positive control transcriptional profile correspond to a statistically significant upregulation in the transcription of REL, and/or a statistically downregulation in the transcription of MAP3K. In other particular embodiments, the transcriptional profile comprises data related to transcription of at least CASP3. In such an embodiment, the positive control is ZPT. In such embodiments, the cosmetic test agent is identified as a skin moisturizing agent if the transcriptional profile of the skin tissue sample and the positive control transcriptional profile correspond to a statistically significant upregulation in the transcription of CASP3. In further particular embodiments, the transcriptional profile comprises data related to transcription of at least ITGB1, TGFBR2. In such an embodiment, the positive control is monoolein. In such embodiments, the cosmetic test agent is identified as a skin moisturizing agent if the transcriptional profile of the skin tissue sample and the positive control transcriptional profile correspond to a statistically significant upregulation in the transcription of ITGB1 and/or TGFBR2. In even further embodiments, the transcriptional profile comprises data related to transcription of at least two genes selected from REL, TGFBR2, MAP3K, CASP3. In such an embodiment, the positive control is olivem 1000. In such embodiments, the cosmetic test agent is identified as a skin moisturizing agent if the transcriptional profile of the skin tissue sample and the positive control transcriptional profile correspond to a statistically significant upregulation in the transcription of REL, TGFBR2, and/or CASP3, and/or a statistically downregulation in the transcription of MAP3K.

An additional embodiment is directed to a screening method for identifying a cosmetic test agent as a skin moisturizing agent to human skin. The method comprises: (a) contacting a skin tissue sample with a cosmetic test agent; (b) generating a transcriptional profile for the skin tissue sample, wherein the transcriptional profiles comprise data related to the transcription of at least two genes selected from TERT, MDM2, LAMC2; (c) comparing the transcriptional profile for the skin tissue sample to a positive control transcriptional profile; and (d) identifying the cosmetic test agent as a skin moisturizing agent for human skin when the transcriptional profile for the skin tissue sample and the positive control transcriptional profile are concordant. A positive control can include, for example, a transcriptional profile of a skin tissue sample treated with a positive control agent such as glycerin, zinc pyrithione (ZPT), monoolein, and olivem 1000. Thus, in some embodiments, the positive control transcriptional profile is a second skin tissue sample contacted with a positive control agent. In such embodiments, the cosmetic test agent is identified as a skin moisturizing agent if the transcriptional profile of the skin tissue sample and the positive control transcriptional profile correspond to a statistically significant upregulation in the transcription of TERT, and/or LAMC2, and/or a statistically downregulation in the transcription of MDM2. In some embodiments, the disclosed genes of interest may serve as to identify cosmetic agents that are skin moisturizing agents to the dry skin of subjects with inherently dry skin exacerbated by seasonal effects (e.g. during the winter season). In certain embodiments, the positive control can be glycerin, ZPT, or monoolein. In particular embodiments, the positive control is glycerin. Importantly, the disclosed unique gene expression signature may serve as indicators of previously unidentified pathways associated with dry skin repair, and thus can provide opportunities for identifying new classes of cosmetic agents.

In more particular embodiments, the transcriptional profile comprises data related to transcription of at least TERT, MDM2. In such an embodiment, the positive control is ZPT. In such embodiments, the cosmetic test agent is identified as a skin moisturizing agent if the transcriptional profile of the skin tissue sample and the positive control transcriptional profile correspond to a statistically significant upregulation in the transcription of TERT, and/or a statistically downregulation in the transcription of MDM2. In further particular embodiments, the transcriptional profile comprises data related to transcription of at least MDM2. In such an embodiment, the positive control is monoolein. In such embodiments, the cosmetic test agent is identified as a skin moisturizing agent if the transcriptional profile of the skin tissue sample and the positive control transcriptional profile correspond to a statistically significant downregulation in the transcription of MDM2.

Generally, the cosmetic test agents identified to be skin moisturizing agents by the presently-disclosed methods may be applied in accordance with cosmetic compositions and formulation parameters well-known in the art. Various methods of treatment, application, regulation, or improvement may utilize the skin care compositions comprising skin-active agents identified according to the inventive methods. In some aspects, the skin care compositions comprising skin-active agents identified according to the inventive methods are applied topically to the desired area of the skin in an amount sufficient to provide effective delivery of the actives. For example, the compositions can be applied directly to the skin or indirectly via the use of an applicator pad or brush, cleansing puff, washcloth, sponge or other implement.

Because of the desirability of providing skin moisturizing benefits to a consumer, it may be beneficial to incorporate cosmetic test agents or compounds identified by one or more of the screening methods described herein into a cosmetic composition suitable for topical application to skin. That is, it may be desirable to include the cosmetic test agent as an ingredient in the cosmetic composition. In certain embodiments, the cosmetic composition may include a dermatological acceptable carrier, the test agent, and one or more optional ingredients of the kind commonly included in the particular cosmetic compositing being provided.

The phrase "dermatologically acceptable carrier", as used herein, means that the carrier is suitable for topical application to the keratinous tissue, has good aesthetic properties, is compatible with the actives in the composition, and will not cause any unreasonable safety or toxicity concerns. Suitable carriers may include water and/or water miscible solvents. The cosmetic skin care composition may comprise from about 1% to about 95% by weight of water and/or water miscible solvent. The composition may comprise from about 1%, 3%, 5%, 10%, 15%, 20%, 25%, 30%, 35%, 40%, 45%, 50%, 55%, 60%, 65%, 70%, 75%, 80%, or 85% to about 90%, 85%, 80%, 75%, 70%, 65%, 60%, 55%, 50%, 45%, 40%, 35%, 30%, 25%, 20%, 15%, 10%, or 5% water and/or water miscible solvents. Suitable water miscible solvents include monohydric alcohols, dihydric alcohols, polyhydric alcohols, glycerol, glycols, polyalkylene glycols such as polyethylene glycol, and mixtures thereof. When the skin care composition is in the form of an emulsion, water and/or water miscible solvents are carriers typically associated with the aqueous phase.

Suitable carriers also include oils. The skin care composition may comprise from about 1% to about 95% by weight of one or more oils. The composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of one or more oils. Oils may be used to solubilize, disperse, or carry materials that are not suitable for water or water soluble solvents. Suitable oils include silicones, hydrocarbons, esters, amides, ethers, and mixtures thereof. The oils may be volatile or nonvolatile.

Suitable silicone oils include polysiloxanes. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.).

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include C4-20 alkyl ethers of polypropylene glycols, and di-C8-30 alkyl ethers. Suitable examples of these materials include PPG-14 butyl ether, PPG-15 stearyl ether, dioctyl ether, dodecyl octyl ether, and mixtures thereof.

The skin care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. Nos. 3,755,560, 4,421,769, and McCutcheon's, Emulsifiers and Detergents, 2010 Annual Ed., published by M. C. Publishing Co. Other suitable emulsifiers are further described in the Personal Care Product Council's International Cosmetic Ingredient Dictionary and Handbook, Thirteenth Edition, 2006, under the functional category of "Surfactants—Emulsifying Agents."

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu. Emulsifiers also include emulsifying silicone elastomers. Suitable silicone elastomers may be in the powder form, or dispersed or solubilized in solvents such as volatile or nonvolatile silicones, or silicone compatible vehicles such as paraffinic hydrocarbons or esters. Suitable emulsifying silicone elastomers may include at least one polyalkyl ether or polyglycerolated unit.

Structuring agents may be used to increase viscosity, thicken, solidify, or provide solid or crystalline structure to the skin care composition. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents.

Polysaccharides and gums may be suitable aqueous phase thickening agents. Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof. Silicone gums are another oil phase structuring agent. Another type of oily phase structuring agent includes silicone waxes. Silicone waxes may be referred to as alkyl silicone waxes which and are semi-solids or solids at room temperature. Other oil phase structuring agents may be one or more natural or synthetic waxes such as animal, vegetable, or mineral waxes.

The compositions of the present invention may contain a variety of other ingredients provided that they do not unacceptably alter the benefits of the invention. When present, compositions of the present invention may contain from about 0.0001% to about 50%; from about 0.001% to about 20%; or, alternately, from about 0.01% to about 10%, by weight of the composition, of the optional components. The amounts listed herein are only to be used as a guide, as the optimum amount of the optional components used in a composition will depend on the specific active selected since their potency does vary considerably. Hence, the amount of some optional components useful in the present invention may be outside the ranges listed herein.

The optional components, when incorporated into the composition, should be suitable for use in contact with human skin tissue without undue toxicity, incompatibility, instability, allergic response, and the like. The compositions of the present invention may include optional components such as anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful skin care actives, which are described in further detail in U.S. application publication No. US2006/0275237A1 and US2004/0175347A1.

The Personal Care Product Council's *International Cosmetic Ingredient Dictionary and Handbook*, Thirteenth Edition, describes a wide variety of non-limiting cosmetic and pharmaceutical ingredients commonly used in the skin care industry, which are suitable optional components for use in the compositions of the present invention. Examples of these ingredient classes include: abrasives, absorbents, aesthetic components such as fragrances, pigments, colorings/colorants, essential oils, anti-caking agents, antifoaming agents, antimicrobials, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners viscosity modifiers, vitamins, and combinations thereof.

The skin care compositions may be generally prepared by conventional methods such as known in the art of making compositions and topical compositions. Such methods typically involve mixing of ingredients in or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (physical stability, chemical stability, photostability, etc.) and/or delivery of active materials.

The compositions may be in various product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks (with and without insoluble sheet), make-up such as foundations, eye liners, and eye shadows, and the like. The composition may be provided in a package sized to store a sufficient amount of the composition for a treatment period. The size, shape, and design of the package may vary widely. Certain package examples are described in U.S. Pat. Nos. D570,707; D391,162; D516,436; D535,191; D542,660; D547,193; D547,661; D558,591; D563,221; 2009/0017080; 2007/0205226; and 2007/0040306.

METHODS

Genomics Method

The description below provides an exemplary method for obtaining a gene expression profile from purified RNA. It is to be appreciated that the method can be readily adapted by an ordinary skilled artisan to account for different amounts and/or instruments from those described in the example.

25 ng of purified RNA is converted to biotin-labeled cRNA copies using the Affymetrix HT 3' IVT Express kit (Cat. #901253) and protocol provided as executed on a Beckman Biomek® FX$^P$ Laboratory Automation Workstation (Beckman Cat. #A31842), or equivalent. In brief, 500 ng of total RNA is reverse-transcribed into cDNA copies using oligo-dT primers and reverse transcriptase followed by second strand synthesis using DNA polymerase I. Following purification, the cDNA library is used as a template for generating biotin-labeled cRNA copies using T7 RNA polymerase and biotinylated dUTP. Biotinylated cRNA is fragmented by limited alkaline hydrolysis and then hybridized overnight to Affymetrix GeneTitan® U219 array plates using the Affymetrix GeneTitan® instrument and protocol provided. Following processing, chip images are converted to numeric data using the PLIER algorithm as executed in the Affymetrix GeneChip Expression Console.

Dryness Grading

The skin on the subject lower leg is graded for dryness by a qualified grader according to the scales below. Visual evaluations is done with the aid of a Luxo Illuminated Magnifying Lamp (Model KFM-1A), which provides 2.75× magnification and has a shadow-free circular fluorescent light source (General Electric Cool White, 22 watt 8" Circline bulb).

| Grade$^a$ | Dryness$^b$ |
| --- | --- |
| 0.0 | Perfect skin. |
| 1.0 | Patches of checking and/or slight powderiness, occasional patches of small scales may be seen, distribution generalized. |
| 2.0 | Generalized slight powderiness, early cracking or occasional small lifting scales may be present. |
| 3.0 | Generalized moderate powderiness and/or moderate cracking and scales. |
| 4.0 | Generalized heavy powderiness and/or heavy cracking and lifting scales. |
| 5.0 | Generalized high cracking and lifting scales, eczematous change |

-continued

| Grade[a] | Dryness[b] |
|---|---|
| | may be present but not prominent, may see bleeding cracks. |
| 6.0 | Generalized severe cracking, bleeding cracks and eczematous changes may be present, large scales may be sloughing off. |

[a]half-unit grades may be used if necessary
[b]'generalized' refers to situations where more than 50% of the application area is affected

EXAMPLES

Example 1

A clinical study was conducted to conduct a genomic evaluation of subjects with inherently dry skin versus subjects with inherently normal moisturized skin in the winter season (phase 1) and summer season (phase 2. The clinical study design for each phase was a leg controlled application test (LCAT) protocol. The phase 2 portion of the test also included a determination of genomic differences between subjects that are treated with a drying agent ("surfactant challenged").

Phase 1 clinical design: human subjects were screened for dry skin score during the winter season (e.g. November-March) in accordance with the dryness grading procedure described herein below. All subjects were pre-conditioned with Olay® soap bar for 7 days (days −7 to −1) followed by a 2 day regression. Subjects were instructed to abstain from washing their legs with any products and from using any leave-on products on their legs during the pretreatment period. Dry Skin Grade measurements and full-thickness skin biopsies were taken on day 1. The full thickness biopsies were later separated into epidermal and dermal sections using laser capture microdissection ("LCM"), and the epidermal section was used for genomic analysis. Subjects with a dry skin score of 2.5 to 4.0 were determined to be subjects with inherently dry skin, while subjects with a dry skin score of less than 1 were determined to be subjects with inherently normal moisturized skin. A cohort of 36 subjects was selected for the inherently dry skin group, while a cohort of 18 subjects was selected for the inherently normal moisturized skin group.

Phase 2 clinical design: human subjects from phase 1 were recalled during the summer season (i.e., June-August) and maintained in their respective cohort groups. A cohort of 29 subjects was recalled for the inherently dry skin group, while a cohort of 12 subjects was recalled for the inherently normal moisturized skin group. All subjects were pre-conditioned with Olay® soap bar for 7 days (days −7 to −1) followed by a 2 day regression. Subjects were instructed to abstain from washing their legs with any products and from using any leave-on products on their legs during the pretreatment period. Dry Skin Grade measurements, full thickness biopsies, and other skin health measurements (e.g., TEWL) were taken on day 1. Subjects with a dry skin score of greater than 4.0 were excluded from biopsies. The full thickness biopsies were later separated into epidermal and dermal sections via LCM, and the epidermal section was used for genomic analysis.

On days 3-7 (5 consecutive days) subjects who have a Dryness Grade less than 3.0 on one or both legs continue on the study, all other subjects were excused from the study. The clinical staff conducted visual grading at a site adjacent to the biopsy site, followed by a surfactant challenge (i.e., treating the site with 1% sodium lauryl sulfate ("SLS") solution and occluding the site with a Hill Top Chamber® brand occlusive patch test system for 30 minutes). Each day the dryness was visually graded prior to the SLS treatment. On day 8 (24 hrs. following Day 7), bio-instruments measures were taken, but biomarkers and biopsies were only taken if the surfactant challenged site has a Dryness Grade below 4.0.

Results: 237 LCM-derived epidermal samples were processed on GeneTitan® U219 chips as described above. Of these, 11 were statistical outliers that were eliminated from the data set. For purposes of statistical treatment, the left and right leg samples from each subject, at each phase of the study, were considered replicates. An ANOVA model was used to determine group differences. At a p value of <0.05, approximately 2465 probes are expected to be significantly different (between any dry vs. normal skin or any study phase comparison) by chance alone. The actual numbers of significantly different probes are shown in Table 1:

TABLE 1

| Comparison | Number of Probes | Significant Beyond Chance |
|---|---|---|
| P1 Dry vs. P1 Healthy | 1865 | No |
| P2 BL Dry vs. P2 BL Healthy | 2259 | No |
| P2 D5 Dry vs. P2 D5 Healthy | 2477 | No |
| P2 BL Dry vs. P1 Day | 16301 | Yes |
| P2 D5 Dry vs. P2 BL Dry | 10696 | Yes |
| P2 BL Healthy vs. P1 Healthy | 12508 | Yes |
| P2 D5 Healthy vs. P2 BL Healthy | 6110 | Yes |

There was no statistically significant difference (beyond chance) for any of the dry skin vs. normal/healthy skin (parallel-group) comparisons; regardless of whether the comparison was from winter samples (Phase 1/P1), summer samples (Phase 2 baseline/P2BL), or summer samples after the 5 day SLS treatment (Phase 2 day 5/P2D5). In contrast, significant differences were seen within the dry skin or normal/healthy skin groups when looking at paired (within-group) comparisons between winter and summer phases of the study or in the summer phase before vs. after SLS treatment. A larger number of significantly different probes were seen with the dry skin group.

A subset of genes (and corresponding proteins) were identified as markers due to their consistent up- or down-regulation across multiple skin conditions or treatments in the dry skin study. The four conditions/treatments studied were:

1. Dry skin vs. Healthy skin in wintertime.
2. Dry skin in wintertime vs. summertime.
3. Dry skin in summertime before vs. after short term surfactant (SLS) treatment.
4. Healthy skin in summertime before vs. after short term surfactant (SLS) treatment.

A list of 37 genes (proteins) were identified that were regulated in at least 2 of the above 3 season or treatment comparisons. These identified entities were then cross compared to a list of 4857 entities that were derived in Pathway Studio® software from an imported list of 6341 probes coordinately and significantly up or down regulated (p<0.05) across each of 5 immune/inflammatory skin diseases (dandruff, eczema, atopic dermatitis, acne, and psoriasis)—the Unhealthy Skin Signature. Of the 37 probes discussed above, 20 were included in the unhealthy skin signature and were excluded. The other 17 probes were therefore uniquely regulated in the dry skin study, but not previously associated with the 5 listed skin diseases.

A direct interactions pathway was then created from the remaining 17 unique probes along with various cellular processes, parameters, and diseases relevant to the dry skin study. These are:

Cellular Processes: Skin Barrier, Keratinization
Skin Diseases: Dry Skin, Skin Tightness
Clinical Parameters: Skin Integrity, Skin Conductance, Epithelial Sloughing, Skin Roughness, and TEWL.

Four of the processes, diseases, and parameters were not linked to any of the 17 probes (epithelial sloughing, skin conductance, skin roughness, and skin tightness). Eight probes directly linked to the cell processes, skin barrier or keratinization, to the disease, dry skin, or to the clinical parameters skin integrity or TEWL were eliminated. The reason for this step was to eliminate from this biomarker listing anything with existing literature documentation of any connection to these processes and parameters relevant to a dry skin condition.

After elimination of the linked probes, the remaining 9 probes and their interconnections remained as potential unique biomarkers of the condition of dry skin or surfactant treatment of dry skin. These 9 biomarker probes may serve as a list of potential novel markers of the dry skin phenotype. Using, generally the previous selection process and statistical analysis, biomarker panels were derived for the following target populations: subjects with inherently dry skin, subjects with inherently dry skin that is further exacerbated by seasonal effects (e.g. the winter season), subjects with inherently dry skin that is further exacerbated by treatment with a drying agent (e.g. a surfactant such as sodium lauryl sulphate (SLS)), subjects with inherently normal moisturized skin but with dry skin caused by seasonal effects, and subjects with inherently normal moisturized skin but with dry skin caused by treatment with a drying agent. Representative data is depicted in FIGS. 1-5.

Example 2

Testing Potential Cosmetic Test Agents

Individual experiments (referred to as batches) will generally comprise 30 to 96 samples analyzed using Affymetrix GeneChip® technology platforms, containing 6 replicates of the vehicle control (e.g., DMSO), 2 replicate samples of a positive control that gives a strong reproducible effect in the cell type used (e.g., all trans-retinoic acid for fibroblast cells), and samples of the test material. Replication of the test material can be done in separate batches due to batch effects. In vitro testing can be performed in 6-well plates to provide sufficient RNA for GeneChip® analysis (2-4 µg total RNA yield/well).

In some instances, human telomerized keratinocytes (tKC) (e.g., from the University of Texas, Southwestern Medical Center, Dallas, Tex.) may be cultured (e.g., in EpiLife® media with 1× Human Keratinocyte Growth Supplement (Invitrogen, Carlsbad, Calif.)) on collagen I coated cell culture flasks and plates. The Keratinocytes can be seeded into 6-well plates at 20,000 cells/cm$^2$ 24 hours before chemical exposure. In some instances, human skin fibroblasts (e.g., BJ cell line from ATCC, Manassas, Va.) can be grown in Eagle's Minimal Essential Medium (ATCC) supplemented with 10% fetal bovine serum (HyClone, Logan, Utah) in normal cell culture flasks and plates (Corning, Lowell, Mass.). The BJ fibroblasts can be seeded into 6-well plates at 12,000 cells/cm2 24 hours before chemical exposure.

The cells (e.g., tKC or BJ fibroblasts) are incubated at 37° C. in a humidified incubator with 5% CO2. At t=−24 hours, the cells can be trypsinized from T-75 flasks and plated into 6-well plates in basal growth medium. At t=0, the media can be removed and replaced with the appropriate dosing solution as per the experimental design. Dosing solutions can be prepared the previous day in sterile 4 ml Falcon snap cap tubes. Pure test materials may be prepared at a concentration of 1-200 µM, and botanical extracts may be prepared at a concentration of 0.001 to 1% by weight of the dosing solution. In certain embodiments, glycerin, ZPT, monoolein, or olivem 1000 can be used as the positive control test agent. After 6 to 24 hours of chemical exposure, cells can be viewed and imaged. The wells can be examined with a microscope before cell lysis and RNA isolation to evaluate for morphologic evidence of toxicity. If morphological changes are sufficient to suggest cytotoxicity, a lower concentration of the test agent can be tested. Cells can then lysed with 350 ul/well of RLT buffer containing β-mercaptoethanol (Qiagen, Valencia, Calif.), transferred to a 96-well plate, and stored at −20° C.

RNA from cell culture batches can isolated from the RLT buffer using Agencourt® RNAdvance Tissue-Bind magnetic beads (Beckman Coulter) according to manufacturer's instructions. 1 µg of total RNA per sample can be labeled using Ambion Message Amp™ II Biotin Enhanced kit (Applied Biosystems Incorporated) according to manufacturer's instructions. The resultant biotin labeled and fragmented cRNA can be hybridized to an Affymetrix HG-U133A 2.0 GeneChip®, which can then washed, stained and scanned using the protocol provided by Affymetrix. Alternatively, cRNA can be analyzed using Affymetix HG-U219 gene arrays.

Examples/Combinations

A. A screening method for identifying a cosmetic test agent as a skin moisturizing agent, the method comprising:
  a. contacting a skin tissue sample with a cosmetic test agent;
  b. generating a transcriptional profile for the skin tissue sample, wherein the transcriptional profile comprises data corresponding to the transcription of at least two genes selected from v-rel avian reticuloendotheliosis viral oncogene homolog gene (REL); integrin beta-1 gene (ITGB1); transforming growth factor beta receptor II gene (TGFBR2); YY1-associated protein 1 gene (YY1AP1); mitogen-activated protein kinase 3 gene (MAP3K); caspase 3, apoptosis-related cysteine peptidase gene (CASP3); telomerase reverse transcriptase gene (TERT); mdm2 p53 binding protein homolog gene (MDM2); and laminin, gamma 2 gene (LAMC2);
  c. comparing the transcriptional profile for the skin tissue sample to at lease one of a positive control transcriptional profile and a negative control transcriptional profile; and
  d. identifying the cosmetic test agent as a skin moisturizing agent when the comparison in (c) corresponds to a change in transcription indicative of moisturization.
B. The method of paragraph A, wherein the skin tissue sample comprises keratinocytes and fibroblasts.
C. The method of paragraph A, wherein the skin tissue sample consists essentially of keratinocytes.
D. The method of paragraph A, wherein the skin tissue sample consists essentially of fibroblasts.

E. The method of any one of paragraphs A to D, wherein the tissue sample is subjected to laser capture microdissection.

F. The method of any one of paragraphs A to E, wherein generating the gene expression profile comprises: i. isolating RNA from the tissue sample, ii. using the isolated RNA to create cRNA, iii. labeling the cRNA with a fluorescent dye, and iv. hybridizing the labeled cRNA to a microarray.

G. The method of any one of paragraphs A to F, wherein the transcriptional profile for the skin tissue sample is compared to a positive control transcriptional profile, and the cosmetic test agent is identified as a skin moisturizing agent for human skin when the transcriptional profile for the skin tissue sample and the positive control transcriptional profile are concordant.

H. The method of any one of paragraphs A to F, wherein the transcriptional profile for the skin tissue sample is compared to a negative control transcriptional profile, and the cosmetic test agent is identified as a skin moisturizing agent for human skin when the transcriptional profile for the skin tissue sample and the negative control transcriptional profile are discordant.

I. The method of any one of paragraphs A to H, wherein the transcriptional profile comprises data corresponding to the transcription of at least two genes selected from REL, ITGB1, TGFBR2, MAP3K, CASP3, TERT, MDM2, LAMC2.

J. The method of paragraph I, wherein the transcriptional profile comprises data corresponding to the transcription of at least two genes selected from REL, ITGB1, TGFBR2, TERT, MAP3K, LAMC2.

K. The method of paragraph J, wherein the transcriptional profile comprises data corresponding to the transcription of at least two genes selected from TERT, MAP3K, LAMC2.

L. The method of paragraph J, wherein the transcriptional profile comprises data corresponding to the transcription of at least two genes selected from REL, ITGB1, TGFBR2.

M. The method of paragraph L, wherein the transcriptional profile comprises data corresponding to the transcription of at least two genes selected from REL, TERT, MDM2, MAP3K, LAMC2.

N. The method of paragraph M, wherein the transcriptional profile comprises data corresponding to the transcription of at least two genes selected from TERT, MAP3K, LAMC2, MDM2.

O. The method of paragraph N, wherein the transcriptional profile comprises data corresponding to the transcription of at least two genes selected from TERT, MDM2, LAMC2.

P. The method of any one of paragraphs A to H, wherein the transcriptional profile comprises data corresponding to the transcription of at least two genes selected from REL, ITGB1, TGFBR2, YY1AP1, MAP3K, CASP3.

Q. The method of paragraph P, wherein the transcriptional profile comprises data related to the transcription of at least REL and MAP3K.

R. The method of paragraph P, wherein the transcriptional profile comprises data related to the transcription of at least CASP3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of formulating a moisturizing skin care composition for human skin, comprising:
    a) contacting a skin tissue sample with a cosmetic test agent;
    b) generating a transcriptional profile for the skin tissue sample, wherein the transcriptional profile comprises data related to the transcription of at least two genes selected from the group consisting of v-rel avian reticuloendotheliosis viral oncogene homolog gene (REL); integrin beta-1 gene (ITGB1); transforming growth factor beta receptor II gene (TGFBR2); YY1-associated protein 1 gene (YY1AP1); mitogen-activated protein kinase 3 gene (MAP3K); caspase 3, apoptosis-related cysteine peptidase gene (CASP3); telomerase reverse transcriptase gene (TERT); mdm2 p53 binding protein homolog gene (MDM2); and laminin, gamma 2 gene (LAMC2);
    c) comparing the transcriptional profile for the skin tissue sample to a positive control transcriptional profile
    d) identifying the cosmetic test agent as a skin moisturizing agent for human skin when the transcriptional profile for the skin tissue sample and the positive control transcriptional profile are concordant; and
    e) combining an effective amount of the skin moisturizing agent with a dermatologically acceptable carrier to produce the skin care composition.

2. The method of claim 1, wherein the skin tissue sample comprises keratinocytes and fibroblasts.

3. The method of claim 1, wherein the tissue sample is subjected to laser capture microdissection.

4. The method of claim 1, wherein generating the gene expression profile comprises: i) isolating RNA from the tissue sample, ii) using the isolated RNA to create cRNA, iii) labeling the cRNA with a fluorescent dye, and iv) hybridizing the labeled cRNA to a microarray.

5. The method of claim 1, wherein the transcriptional profile comprises data related to the transcription of at least two genes selected from the group consisting of REL, ITGB1, TGFBR2, YY1AP1, MAP3K, CASP3.

6. The method of claim 1, wherein the transcriptional profile comprises data corresponding to the transcription of at least two genes selected from REL, ITGB1, TGFBR2, TERT, MAP3K, LAMC2.

7. The method of claim 6, wherein the transcriptional profile comprises data corresponding to the transcription of at least two genes selected from the group consisting of REL, ITGB1, TGFBR2.

8. The method of claim 1, wherein the transcriptional profile comprises data corresponding to the transcription of at least two genes selected from the group consisting of REL, ITGB1, TGFBR2, YY1AP1, MAP3K, CASP3.

* * * * *